United States Patent

Hadwen

(10) Patent No.: US 9,662,651 B2
(45) Date of Patent: May 30, 2017

(54) ACTIVE MATRIX DEVICE AND METHOD OF DRIVING THE SAME

(71) Applicant: Sharp Kabushiki Kaisha, Osaka (JP)

(72) Inventor: Benjamin James Hadwen, Oxford (GB)

(73) Assignee: Sharp Microfluidic Solutions Limited, Oxford (GB)

(*) Notice: Subject to any disclaimer, the term of this patent is extended or adjusted under 35 U.S.C. 154(b) by 322 days.

(21) Appl. No.: 14/620,407

(22) Filed: Feb. 12, 2015

(65) Prior Publication Data

US 2015/0158028 A1 Jun. 11, 2015

Related U.S. Application Data

(62) Division of application No. 13/447,379, filed on Apr. 16, 2012, now Pat. No. 8,981,789.

(51) Int. Cl.
*B01L 3/00* (2006.01)
*G01N 27/447* (2006.01)
(Continued)

(52) U.S. Cl.
CPC ..... *B01L 3/502792* (2013.01); *B01L 3/50273* (2013.01); *B01L 3/502707* (2013.01);
(Continued)

(58) Field of Classification Search
CPC ......... B01L 2200/143; B01L 2200/148; B01L 2300/0816; B01L 2300/0819; B01L 2400/0427; B01L 3/502707; B01L 3/50273; B01L 3/502792; B01L 2400/0421; B01L 2300/024; B01L 2200/10; G01N 27/4163; G01N 27/44791; G01R 31/12; G06F 3/0412; G02B 26/005
See application file for complete search history.

(56) References Cited

U.S. PATENT DOCUMENTS

| 4,685,086 A | 8/1987 | Tran |
| 6,565,727 B1 | 5/2003 | Shenderov |
| (Continued) | | |

FOREIGN PATENT DOCUMENTS

EP 2 404 675 A1 1/2012

OTHER PUBLICATIONS

Co-pending U.S. Appl. No. 13/447,379, filed Apr. 16, 2012.
(Continued)

*Primary Examiner* — Jennifer Wecker
(74) *Attorney, Agent, or Firm* — Renner, Otto, Boisselle & Sklar, LLP

(57) ABSTRACT

An active matrix electrowetting on dielectric (AM-EWOD) device includes a plurality of array elements configured to manipulate one or more droplets of fluid on an array, each of the array elements including a corresponding array element circuit. Each array element circuit includes a top substrate electrode and a drive electrode between which the one or more droplets may be positioned, with an insulator layer being interposed between the one or more droplets and the drive electrode; and write circuitry configured to write data to the array element. At least some of the array element circuits include measure circuitry configured to detect a pinhole defect in the insulator layer.

8 Claims, 18 Drawing Sheets

(51) Int. Cl.
*G02B 26/00* (2006.01)
*G01N 27/416* (2006.01)
*G01R 31/12* (2006.01)
*G06F 3/041* (2006.01)

(52) U.S. Cl.
CPC ... *G01N 27/4163* (2013.01); *G01N 27/44791* (2013.01); *B01L 2200/10* (2013.01); *B01L 2200/143* (2013.01); *B01L 2200/148* (2013.01); *B01L 2300/024* (2013.01); *B01L 2300/0816* (2013.01); *B01L 2300/0819* (2013.01); *B01L 2400/0421* (2013.01); *B01L 2400/0427* (2013.01); *G02B 26/005* (2013.01); *G06F 3/0412* (2013.01)

(56) References Cited

U.S. PATENT DOCUMENTS

| | | | |
|---|---|---|---|
| 6,911,132 B2 | 6/2005 | Pamula et al. | |
| 7,163,612 B2 | 1/2007 | Sterling et al. | |
| 7,329,545 B2 | 2/2008 | Pamula et al. | |
| 2004/0055891 A1* | 3/2004 | Pamula | B01F 11/0071 205/98 |
| 2012/0169636 A1* | 7/2012 | Liu | G06F 3/0412 345/173 |
| 2012/0268804 A1* | 10/2012 | Hadwen | B01L 3/502792 359/290 |

OTHER PUBLICATIONS

R.B. Fair, "Digital Microfluidics: is a true lab-on-a-chip possible?", Microfluid Nanofluid (2007) 3:245-281.
Cooney et al., "Electrowetting droplet microfluidics on a single planar surface", Microfluid Nanofluid (2006) 2:435-446.
Restriction Requirement for U.S. Appl. No. 13/447,379 mailed Mar. 11, 2014.

\* cited by examiner

ACTIVE MATRIX DEVICE AND METHOD OF DRIVING THE SAME

TECHNICAL FIELD

The present invention relates to active matrix arrays and elements thereof. In a particular aspect, the present invention relates to digital microfluidics, and more specifically to an Active Matrix Electrowetting-On-Dielectric (AM-EWOD) device. Electrowetting-On-Dielectric (EWOD) is a known technique for manipulating droplets of fluid on an array. Active Matrix EWOD (AM-EWOD) refers to implementation of EWOD in an active matrix array, for example by using thin film transistors (TFTs). The invention further relates to methods of driving such a device.

BACKGROUND ART

Electrowetting on dielectric (EWOD) is a well known technique for manipulating droplets of fluid by application of an electric field. It is thus a candidate technology for digital microfluidics for lab-on-a-chip technology. An introduction to the basic principles of the technology can be found in "Digital microfluidics: is a true lab-on-a-chip possible?", R. B. Fair, Microfluid Nanofluid (2007) 3:245-281).

FIG. 1 shows a part of an EWOD device in cross section. The device includes a lower substrate 72 the uppermost layer of which is formed from a conductive material which is patterned so that a plurality of conductive electrodes 38 (e.g., 38A and 38B in FIG. 4) are realised. These may be termed the EW drive elements. A droplet 4, consisting of an ionic material is constrained in a plane between the lower substrate 72 and a top substrate 36. A suitable gap between the two substrates may be realised by means of a spacer 32, and a non-ionic liquid 34 (e.g. oil) may be used to occupy the volume not occupied by the liquid droplet 4. An insulator layer 20 disposed upon the lower substrate 72 separates the conductive electrodes 38A, 38B from a hydrophobic surface of a hydrophobic layer 16 upon which the liquid droplet 4 sits with a contact angle 6 represented by θ. On the top substrate 36 is another hydrophobic layer 26 with which the liquid droplet 4 may come into contact. Interposed between the top substrate 36 and the hydrophobic layer 26 is a top substrate electrode 28. In operation, voltages, termed the EW drive voltages, (e.g. $V_T$, $V_O$ and $V_{OO}$) may be externally applied to different electrodes (e.g. drive element electrodes 28, 38A and 38B, respectively). The hydrophobicity of the hydrophobic surface of the layer 16 can be thus controlled, thus facilitating droplet movement in the lateral plane between the two substrates 72 and 36.

U.S. Pat. No. 6,565,727 (Shenderov, issued May 20, 2003) discloses a passive matrix EWOD device for moving droplets through an array.

U.S. Pat. No. 6,911,132 (Pamula et al, issued Jun. 28, 2005) discloses a two dimensional EWOD array to control the position and movement of droplets in two dimensions.

U.S. Pat. No. 6,565,727 further discloses methods for other droplet operations including the splitting and merging of droplets and the mixing together of droplets of different materials. In general the voltages required to perform typical droplet operations are relatively high. Values in the range 20 volts (V)-60V are quoted in the prior art (e.g. U.S. Pat. No. 7,329,545 (Pamula et al., issued Feb. 12, 2008)). The value required depends principally on the technology used to create the insulator and hydrophobic layers.

In practise the creation of a suitable insulator layer 20, of sufficiently high quality to facilitate mass production of EWOD devices, can often prove challenging. A suitable, high quality insulator layer must be resilient to electrical breakdown and suitably non-porousso such that ions from the liquid droplet 4 are unable to traverse through the insulator layer under the action of the electric field. In practise it is difficult to fabricate insulator layers where this is always achieved over every part of every electrode 38. Typically insulator layers may suffer from "insulator pinhole defects" in the insulator layer at a few discrete locations within the device. At these locations dielectric breakdown may then occur within the device. Often, the occurrence of an insulator pinhole defect may only become apparent when a liquid droplet 4 comes to reside at the location of the insulator pinhole defect and when the electrode in that location is an actuated state such that an electric field is developed across the insulator layer. Under these circumstances mobile ions from the liquid droplet 4 may traverse through the liquid leading to electrolysis of the liquid, usually at the interface between the liquid droplet 4 and the bottom substrate 72. The occurrence of electrolysis may cause damage to the device and may compromise the chemistry of the liquid droplet 4. In general in EWOD device implementations it is very difficult to determine if, when and where electrolysis due to insulator pinhole defects occurs without viewing the device optically (e.g. through a microscope).

"Electrowetting droplet microfluidics on a single planar surface", Microfluid Nanofluid (2006) 2:435-446 (Cooney et al.) describes how an EWOD device may be protected from damage due to electrolysis at the site of insulator pinhole defects by current limiting the power supply used to supply the EWOD drive voltage to 1 microampere (μA).

U.S. Pat. No. 7,163,612 (J. Sterling et al.; issued Jan. 16, 2007) describes how TFT based electronics may be used to control the addressing of voltage pulses to an EWOD array by using circuit arrangements very similar to those employed in AM display technologies.

The approach of U.S. Pat. No. 7,163,612 may be termed "Active Matrix Electrowetting on Dielectric" (AM-EWOD). There are several advantages in using TFT based electronics to control an EWOD array, namely:

Driver circuits can be integrated onto the AM-EWOD array substrate.

TFT-based electronics are well suited to the AM-EWOD application. They are cheap to produce so that relatively large substrate areas can be produced at relatively low cost TFTs fabricated in standard processes can be designed to operate at much higher voltages than transistors fabricated in standard CMOS processes. This is significant since many EWOD technologies require EWOD actuation voltages in excess of 20V to be applied.

A disadvantage of U.S. Pat. No. 7,163,612 (J. Sterling et al.; issued Jan. 16, 2007) is that it does not disclose any circuit embodiments for realising the TFT backplane of the AM-EWOD.

EP2404675 (Hadwen et al.; published Jan. 11, 2012) describes array element circuits for an AM-EWOD device. Various methods are described for programming and applying an EWOD actuation voltage to the EWOD drive electrode. The voltage write function described includes a memory element of standard means, for example based on Dynamic RAM (DRAM) or Static RAM (SRAM) and input lines for programming the array element. EP2404675 also describes how an impedance sensing function can be incorporated into the array element.

A potential disadvantage of AM-EWOD in general is that the EWOD actuation voltage that can be supplied is limited to the maximum voltage rating of the TFTs. High voltage operation of TFTs may result in device degradation or failure as is well known. Therefore in order to achieve sufficient EWOD actuation, the total capacitance of the insulator layer and hydrophobic layer cannot be designed to be too small. This in effect constrains the maximum thickness of insulator layer that can be used. Therefore attempting to improve the device reliabililty by the use of thicker insulator layers (which may have a lower occurrence of insulator pinhole defects) is impractical because the drive voltage cannot be increased accordingly due to the operating limit of the TFTs.

U.S. Pat. No. 4,685,086 (Tran, published Aug. 4, 1987) describes a circuit for detecting a short circuit in an SRAM memory cell. This includes means for connecting the nodes of the memory cell to the gates of pulldown transistors. The pulldown transistors perform a level shifting function to produce a voltage pattern that is dependent on whether the memory cell is functioning correctly or not.

SUMMARY OF INVENTION

In accordance with an aspect of the invention, an active matrix electrowetting on dielectric (AM-EWOD) device is provided which includes a plurality of array elements configured to manipulate one or more droplets of fluid on an array, each of the array elements including a corresponding array element circuit; each array element circuit including a top substrate electrode and a drive electrode between which the one or more droplets may be positioned, with an insulator layer being interposed between the one or more droplets and the drive electrode; and write circuitry configured to write data to the array element. At least some of the array element circuits include measure circuitry configured to detect a pinhole defect in the insulator layer.

In accordance with another aspect, the measure circuitry in an array element is configured to measure a resistance of the insulator layer to detect a pinhole defect in the insulator layer.

According to another aspect, the measure circuitry in an array element circuit is configured to measure a leakage of charge from the drive electrode through the insulator layer in order to detect the pinhole defect.

According to another aspect, the measure circuitry in an array element is configured to measure an RC time constant associated with a leakage of charge from the drive electrode through the insulator layer in order to detect the pinhole defect.

In accordance with another aspect, the measure circuitry is configured to make multiple measurements of a voltage of the drive electrode at different sampling times following data being written to the array element in order to detect and classify the pinhole defect.

In yet another aspect, the measure circuitry relies on presence of the one or more droplets in the array element in order to detect the pinhole defect.

According to still another aspect, the write circuitry includes an SRAM circuit for storing the data written to the array element, and a selection circuit for selectively connecting an output of the SRAM circuit to the drive electrode to write the stored data to the drive electrode and subsequently disconnecting the output of the SRAM from the drive electrode in order that leakage of charge from the drive electrode is primarily due to leakage via a pinhole defect in the insulator layer; and the measure circuitry samples the voltage of the drive electrode following being disconnected from the output of the SRAM in order to detect the pinhole defect in the insulator layer.

According to still another aspect, the data to be written to the array element is stored in the SRAM circuit via a data line, and an output of the measure circuitry is output from the array element via an output line.

In accordance with another aspect, the data line and output line are common to a plurality of the array elements within a same column of the array.

According to another aspect, the data line and the output line are the same line.

In yet another aspect, the write circuitry is configured to develop an AC voltage between the bottom electrode and top electrode to actuate electro-wetting manipulation of the one or more droplets, and a DC voltage in order for the measure circuitry to detect the pinhole defect in the insulator layer.

According to another aspect, the write circuitry is configured to develop the DC voltage in order for the measure circuitry to detect the pinhole defect in the insulator layer without necessitating rewriting of write data to the array element.

According to yet another aspect, the write circuitry and the measure circuitry share a common inverter.

In still another aspect, the write circuitry and the measure circuitry share a common switch element used to write data from an input/output line to the array element, and to output an output of the measure circuitry from the array element to the same input/output line.

In accordance with another aspect, the write circuitry includes a DRAM circuit for writing a voltage to the drive electrode, and the measure circuitry samples the voltage written to the drive electrode in order to detect the pinhole defect in the insulator layer.

According to another aspect, the array elements each further comprising a droplet sensor circuit for sensing a presence of the one or more droplets of fluid.

According to still another aspect, the device includes a computer controller configured to compute a route for the one or more droplets of fluid to be manipulated on the array accounting for the presence of pinhole defects in the insulator layer as determined via the measure circuitry in the at least some of the array elements.

In yet another aspect of the invention, a method is provided in which the integrity of the insulator layer is checked using the measure circuitry in the array elements to detect pinhole defects in the insulator layer prior to an assay being undertaken with the device.

According to another aspect, the method includes monitoring an evolution of pinhole defects in the insulator layer by continuous or repeated checking of the insulator layer over time using the measure circuitry in the array elements to detect pinhole defects.

In accordance with another aspect, the method includes varying the voltage which is written to the drive electrodes in the array elements in order to detect the pinhole defect in the insulator layer.

According to still another aspect, the method includes using the measure circuitry in the array elements to detect pinhole defects in the insulator layer without rewriting write data to the array element.

In still another aspect, the method includes detecting pinhole defects in the insulator layer of the array elements with the measure circuitry, and determining a route by which to manipulate the one or more droplets taking into account the detected pinhole defects.

In accordance with another aspect, the method includes creating a map of array elements which include a pinhole defect.

In accordance with another aspect, the method includes using the measure circuitry in the array elements to detect pinhole defects in the insulator layer in the factory of manufacture.

According to still another embodiment, the method includes using the measure circuitry in the array elements to verify operation of the write circuitry in the array elements.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF DRAWINGS

In the annexed drawings, like references indicate like parts or features.

DESCRIPTION OF REFERENCE NUMERALS

Figure 1:
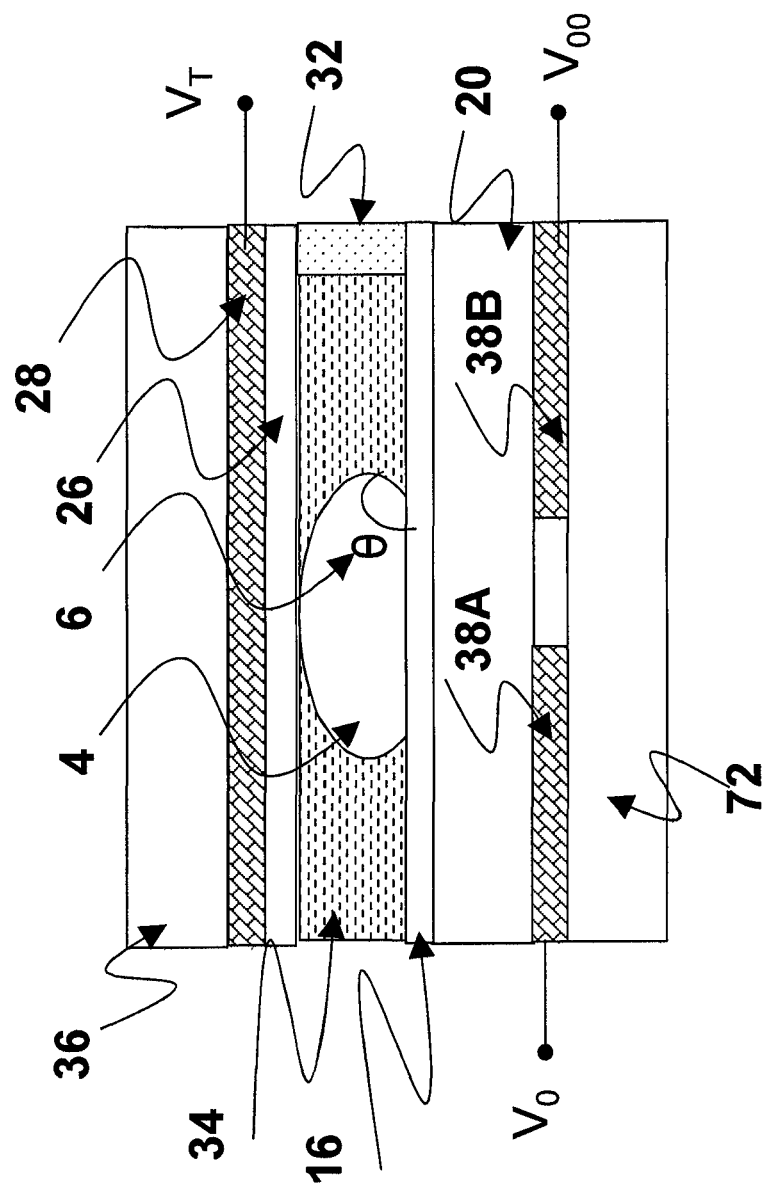
FIG. 1 shows prior art: an EWOD device in cross-section.

4 Liquid droplet
6 Contact angle θ
16 Hydrophobic layer
20 Insulator layer
26 Hydrophobic layer
28 Electrode
32 Spacer
34 Non-ionic liquid
36 Top substrate
38 Electrode
42 Electrode array
72 Substrate
74 Thin film electronics
76 Row driver circuit
78 Column driver circuit
80 Serial interface
82 Connecting wires
83 Voltage supply interface
84 Array element circuit
86 Column detection circuit
88 SRAM circuit
90 Transistor
94 Capacitor
96 Inverter
98 Transistor
99 Capacitor
100 Component representing combination of insulator and hydrophobic layers
102 Droplet sensor circuit
104 Inverter
106 Inverter
107 Transistor
108 Transistor
110 External control electronics
112 Computer controller
114 Array element containing insulator pinhole defect
120 Voltage write circuitry
122 Analogue switch
124 Analogue switch

DETAILED DESCRIPTION OF INVENTION

Figure 2:
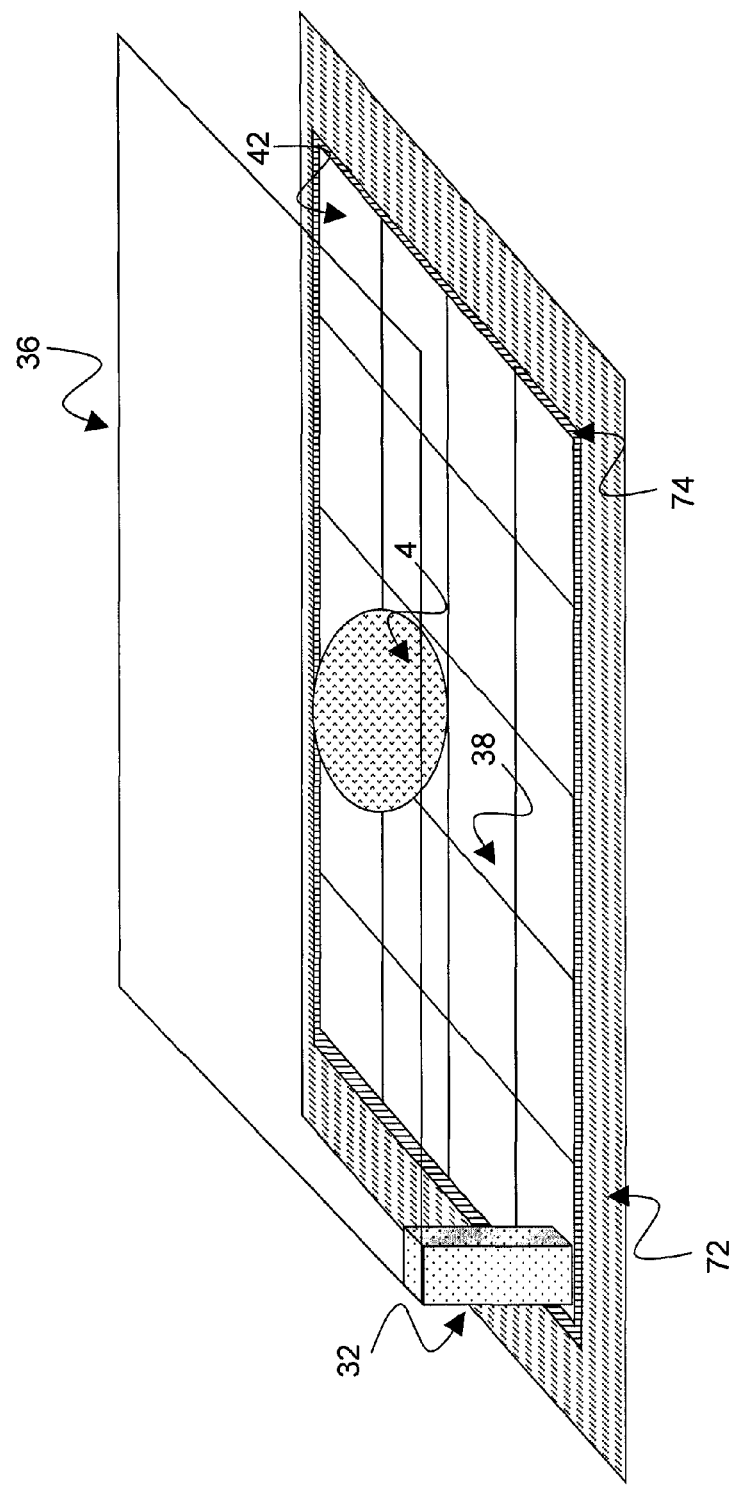
FIG. 2 shows an AM-EWOD device in schematic perspective in accordance with an exemplary embodiment of the invention.

Referring to FIG. 2, shown is an AM-EWOD device in accordance with an exemplary embodiment of the present invention. The AM-EWOD device has a lower substrate 72 with thin film electronics 74 disposed upon the substrate 72. The thin film electronics 74 are arranged to drive array element electrodes, e.g. 38. A plurality of array element electrodes 38 are arranged in an electrode array 42, having M×N array elements where M and N may be any number. An ionic liquid droplet 4 is enclosed between the substrate 72 and the top substrate 36, although it will be appreciated that multiple liquid droplets 4 can be present without departing from the scope of the invention.

Figure 3:
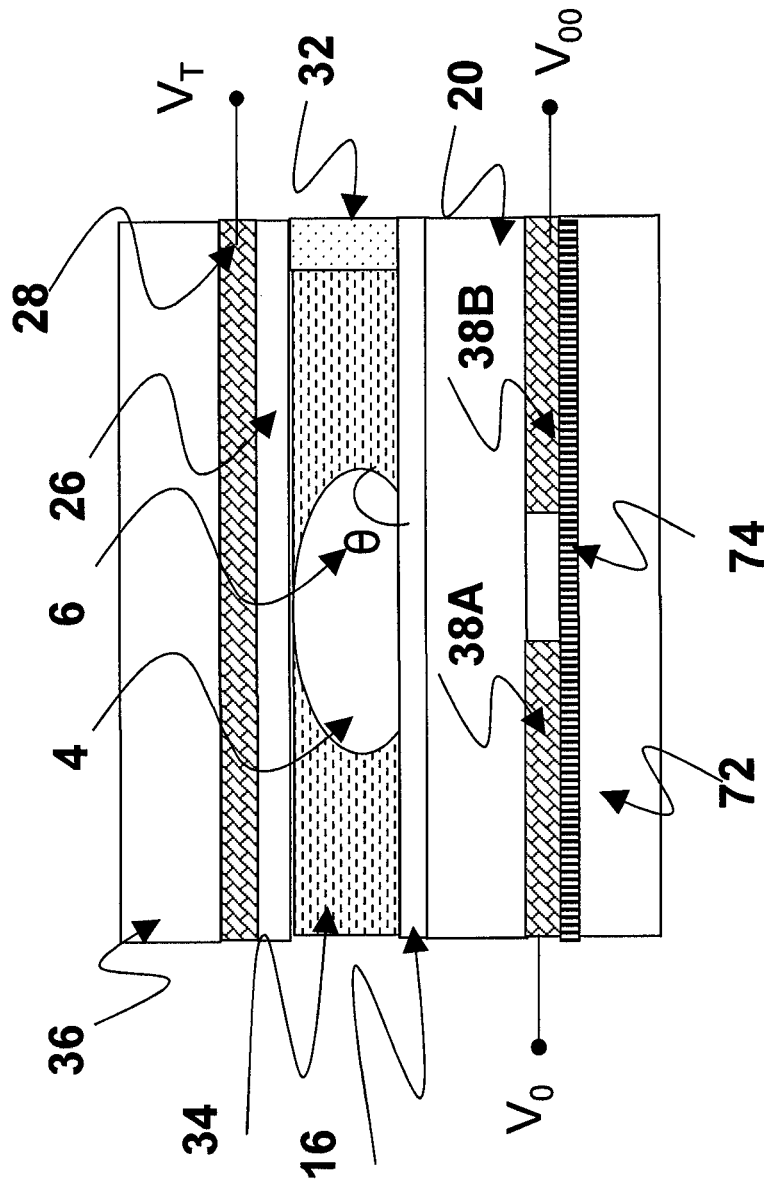
FIG. 3 shows a cross section through some of the array elements of the device.

FIG. 3 shows a pair of the array elements in cross section. The device is in essence identical to that of the conventional art shown in FIG. 1 with the exception that the lower substrate 72 has the thin-film electronics 74 disposed thereon. The uppermost layer of the lower substrate 72 (which may be considered a part of the thin film electronics layer 74) is patterned so that a plurality of electrodes 38 (e.g., 38A and 38B in FIG. 4) are realised. These may be termed the EW drive elements. The term EW drive element may be taken in what follows to refer both to the electrode 38 associated with a particular array element, and also to the node of an electrical circuit directly connected to this electrode 38.

Figure 4:
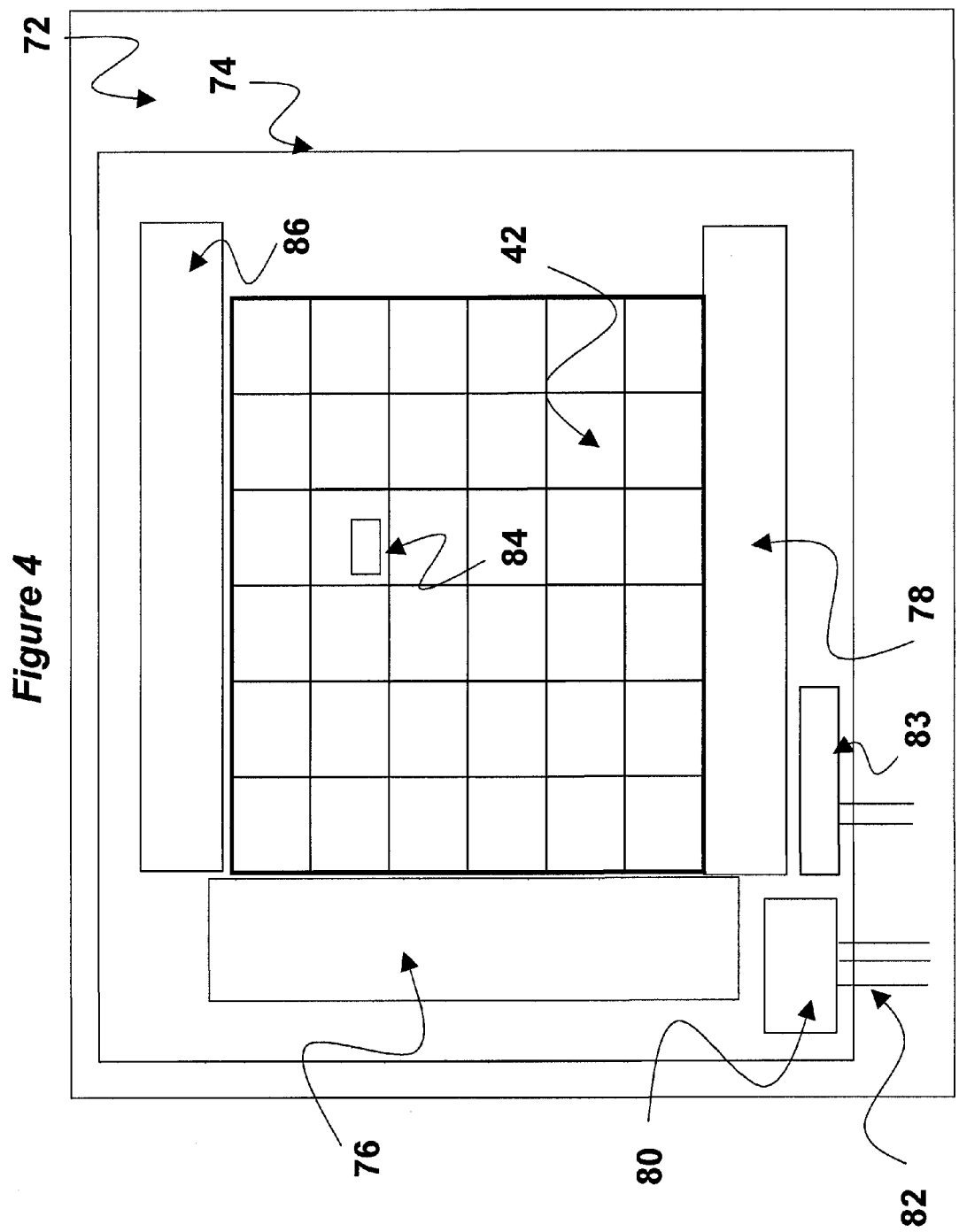
FIG. 4 shows the arrangement of thin film electronics in the device.

The arrangement of thin film electronics 74 upon the substrate 72 is shown in FIG. 4. Each array element of the electrode array 42 contains an array element circuit 84 for controlling the electrode potential of a corresponding electrode 38. Integrated row driver 76 and column driver 78 circuits are also implemented in thin film electronics to supply control signals to the array element circuits 84.

A serial interface 80 may also be provided to process a serial input data stream and write the required voltages to the electrode array 42. A voltage supply interface 83 provides the corresponding supply voltages, top substrate drive voltages, etc., as described herein. The number of connecting wires 82 between the array substrate 72 and external drive electronics, power supplies, etc. (not shown) can be made relatively few, even for large array sizes.

At least some (i.e., one or more) of the array element circuits 84 also contain a means for sensing insulator pinhole defects in the insulator layer 20 and generating a sensor output signal representative of the resistance of the insulator layer 20 as further described herein. A column detection circuit 86 is also provided for processing and read-out of the sensor output signal.

Figure 5:
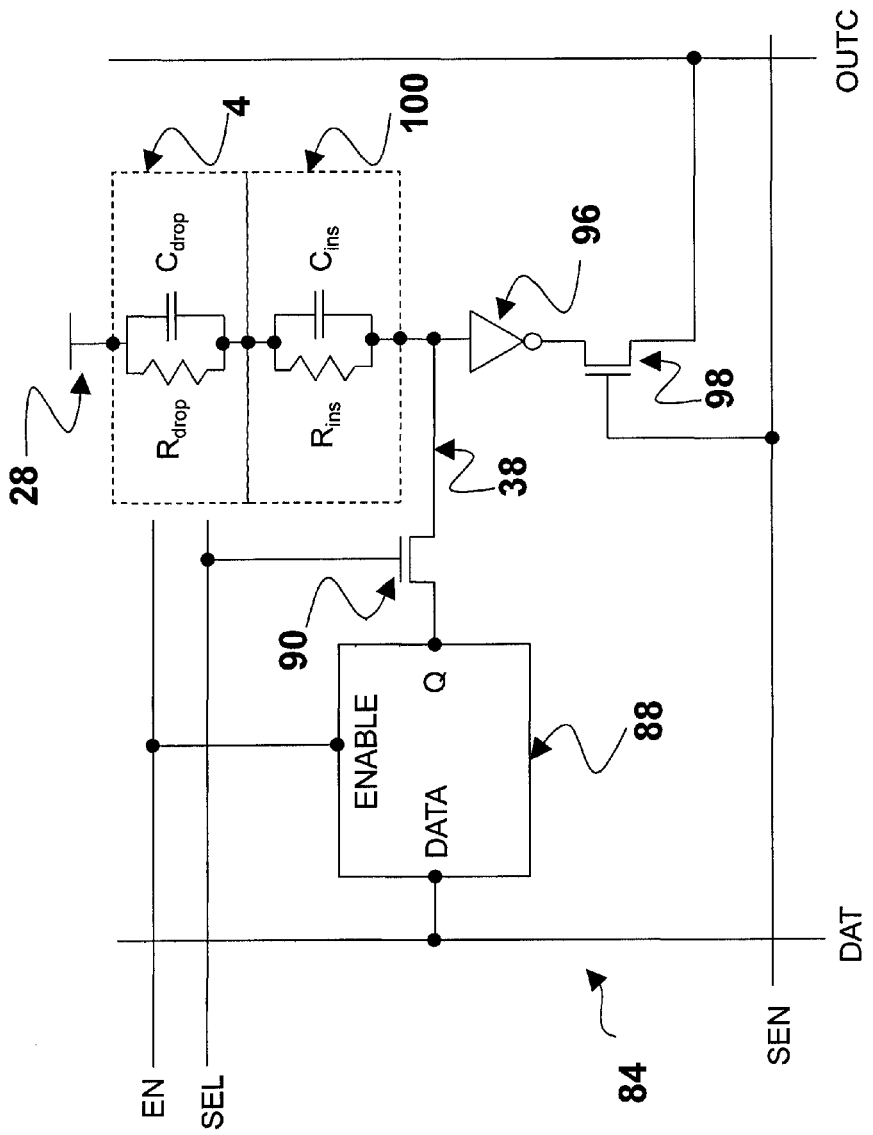
FIG. 5 shows the array element circuit 84 of the first embodiment.

An array element circuit 84 according to a first embodiment is shown in FIG. 5. The remainder of the AM-EWOD device is of the standard construction previously described and includes a top substrate 36 having an electrode 28.

Each array element circuit 84 contains:
An SRAM circuit 88 of standard construction, having DATA and ENABLE inputs and an output Q.
A switch transistor 90
An inverter 96
A switch transistor 98

In considering the operation of the circuit one should take into account the load present at the electrode 38. This load is a function of the combination of the insulator 20 and hydrophobic layers 16, 26 (represented collectively as 100), in series with the liquid droplet 4 (when present). The combination 100 of the insulator and hydrophobic layers may be represented as a resistor $R_{ins}$ in parallel with a capacitor $C_{ins}$. The liquid droplet 4 may also be represented to a good approximation by a capacitor $C_{drop}$ in parallel with a resistor $R_{drop}$.

The array element circuit 84 is connected as follows:
The DATA input of the SRAM circuit 88 is connected to an input line DAT which may be common to all elements within the same column of the array. The ENABLE input of the SRAM circuit 88 is connected to an input line EN which may be common to all elements within the same row of the array 42. The output Q of the SRAM circuit 88 is connected to the source of transistor 90, which serves as a selection circuit for selectively writing the output of the SRAM circuit 88 to the electrode 38. The gate of transistor 90 is connected to a select signal line SEL which may be common to all elements within the same row of the array 42. The drain of transistor 90 is connected to the electrode 38 and to the input of inverter 96. The output of the inverter 96 is connected to the drain of transistor 98. The gate of transistor 98 is connected to the sensor enable (or sense signal) input line SEN which may be common to all elements within the same row of the array 42. The source of transistor 98 is connected to the output line OUTC which may be common to all array elements within the same column of the array 42.

Figure 6:
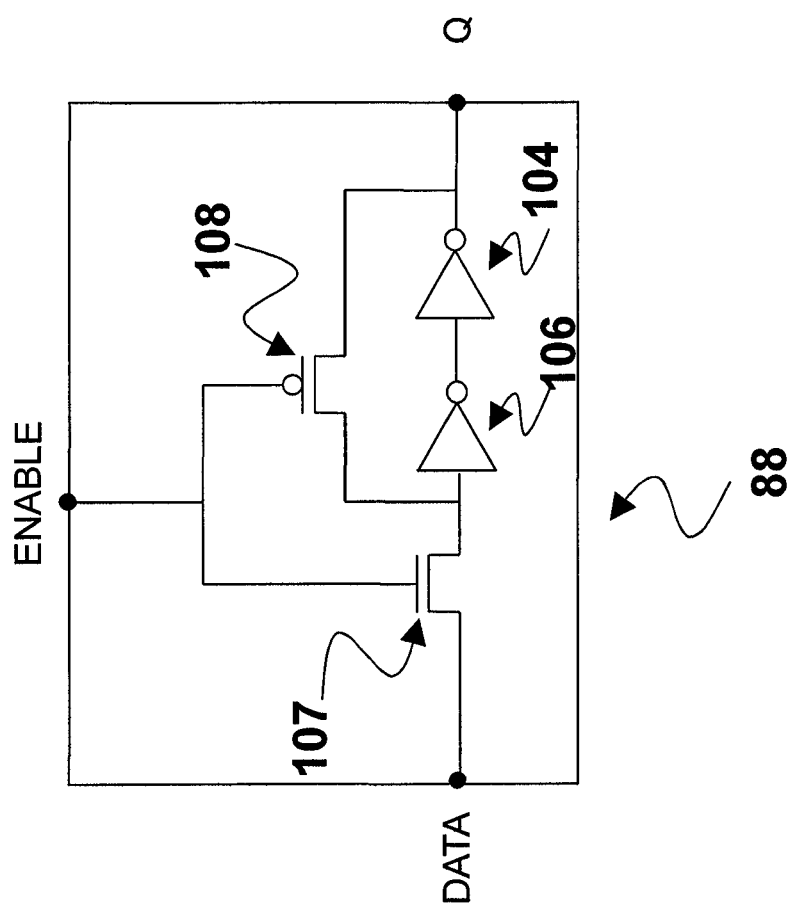
FIG. 6 shows an example design of SRAM circuit included in the array element circuit 84 of the first embodiment

An known examplary implementation of the SRAM circuit 88 is shown in FIG. 6 and includes:
An inverter 104
An inverter 106
A switch transistor of n-type 107
A switch transistor of p-type 108

The source of transistor 107 is connected to the input connection DATA. The gate of transistor 107 is connected to the gate of transistor 108 and to the input ENABLE. The drain of transistor 107 is connected to the source of transistor 108 and to the input of inverter 106. The output of inverter 106 is connected to the input of inverter 104. The output of inverter 104 is connected to the drain of transistor 108 and to the output connection Q.

The SRAM circuit 88 operates as follows, having a write operation and a hold operation. During a write operation, the ENABLE signal on line EN is switched high so that transistor 107 is turned on and transistor 108 is turned off. The voltage level on DATA is then present at the input of inverter 106. Following the completion of the write operation the ENABLE signal is switched low and the SRAM element 88 performs a hold operation. During the hold operation transistor 107 is turned off and transistor 108 is turned on. The voltage written to the input of inverter 106 is twice inverted and thus replicated at the output of inverter 104. This is fed-back to the input of inverter 106. The SRAM circuit 88 thus operates as a memory cell, maintaining the output level at Q to the last programmed state, irrespective of the input DATA.

A number of variants to the circuit of FIG. 6 exist which are also very well known. For example, transistor 108 could be replaced by a n-type transistor whose gate is connected to an additional input ENABLEB which is driven by the inverse of the voltage signal used to drive the input ENABLE. Another alternative is to replace transistors 107 and 108 by analogue switches of standard construction. Finally it may be noted that a second output QB of the SRAM circuit 88 can be taken from the output of inverter 106, whose value is always the logical inverse of output Q.

The operation of the array element circuit 84 of FIG. 5 is described as follows:
The array element circuit 84 performs two functions:
(1) A write operation: using write circuitry as described herein to write an EWOD voltage to the electrode 38
(2) A measure operation: using measure circuitry as described herein to measure the electrical properties of the insulator and hydrophobic layer combination 100, and thus determine or detect whether insulator pinhole defects are present in the insulator layer 20

In order to perform the write operation, a data voltage is programmed to the SRAM circuit 88. The desired voltage corresponds to either logic high or logic low level and is loaded onto the data line DAT via the column driver circuit 78. A voltage pulse is then applied to the enable line EN via the row driver circuit 76. The SRAM circuit 88 is then programmed and the programmed state will continue to be held after EN is taken low.

Whilst the select signal SEL provided by the row driver circuit 76 is at logic high level, transistor 90 is turned on and the output Q of the SRAM element 88 is written to the electrode 38. It is possible for the select signal SEL to be either high or low whilst the SRAM element 88 is being re-programmed.

Figure 7:
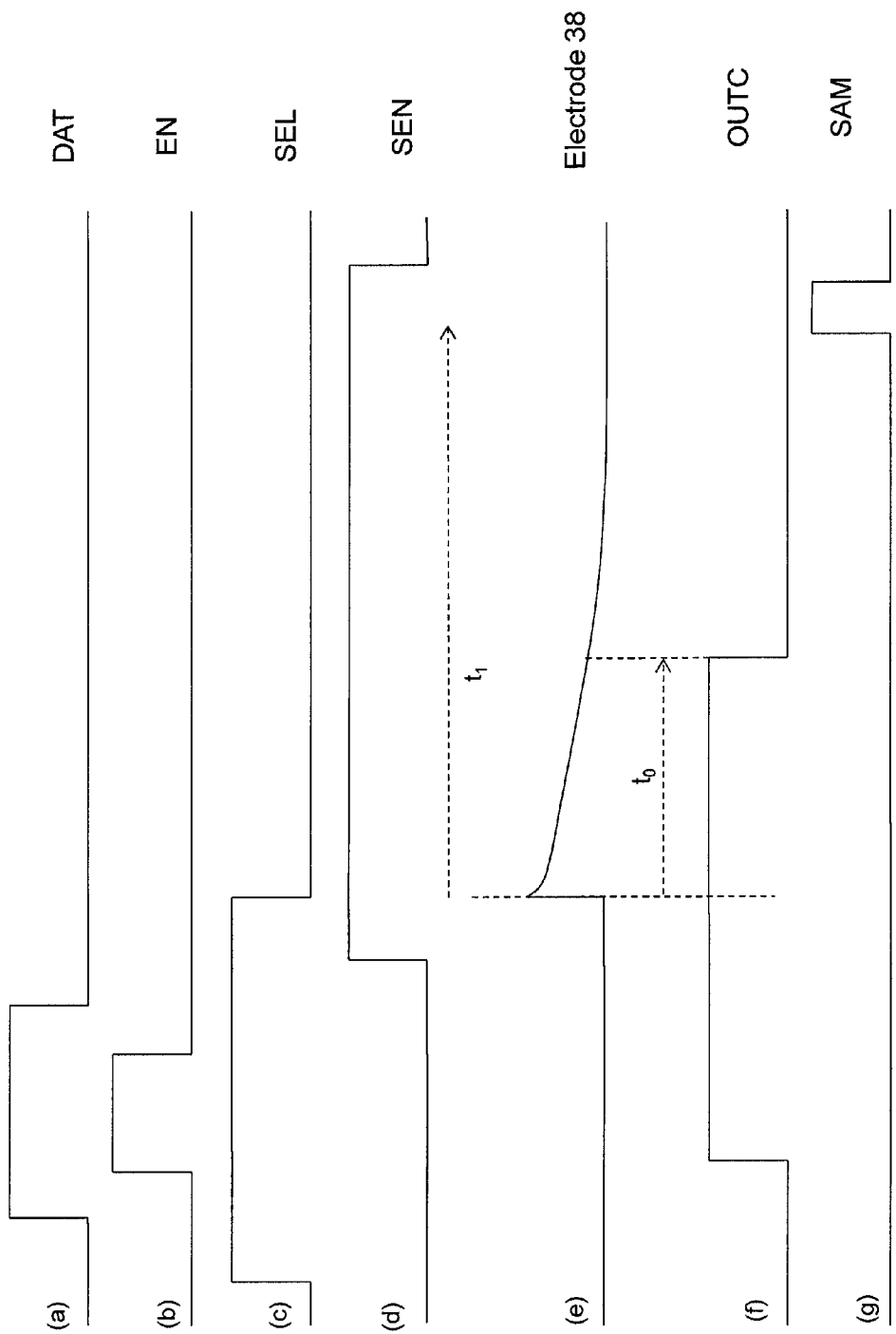
FIG. 7 shows voltage timing signals according to operation of the first embodiment in the case where the insulator contains an insulator pinhole defect.

FIG. 7 shows a timing diagram of the voltage signals for performing the measure operation. We firstly describe operation of the array element circuit 84 in the case where a liquid droplet 4 is present at the location of the electrode 38 and the insulator layer 20 at the array element contains an insulator pinhole defect, as follows:
(1) Initially the electrode 38 is written to voltage high level as described above (FIGS. 7(a)-7(c)). The top electrode 28 is maintained at voltage low level so that a DC electric field between the respective electrodes is maintained across the series combination of the liquid droplet 4 and the hydrophobic layer and insulator layer combination 100.

(2) The applied voltage signal SEL is then taken low by the row driver circuit 76. This disconnects the output Q of the SRAM circuit 88 from the electrode 38. In the event an insulator pinhole defect is present in the insulator layer 20, from the time that select signal SEL is taken low the charge associated with the voltage programmed to the electrode 38 will start to leak away. If one assumes leakage due to circuit components (the switch TFT 90 and inverter 96) to be low, the rate of decay depends on the RC components comprising the load, and thus is primarily due to leakage via the insulator pinhole defect. For simplicity of explanation one may assume the droplet 4 to be relatively conductive such that $R_{drop}$ and $C_{drop}$ may be replaced by a short circuit. In this case the time evolution of the voltage $V_{EW}(t)$ at the electrode 38 decays exponentially as shown in FIG. 7 and approximately in accordance with the equation:

$$V_{EW}(t) = V_{EW} \exp\left(\frac{-t}{R_{ins}C_{ins}}\right) \quad \text{(equation 1)}$$

where $V_{EW}$ is the voltage that was written to the electrode 38 and the voltage of the top substrate electrode 28 is 0V. As the voltage of the electrode 38 decays (FIG. 7(e)), it may reach a point at which it causes the inverter 96 to change state. Initially (i.e. at the time SEL was taken low), the output OUTC was at voltage high level (FIG. 7(f)). If we assume the inverter 96 will change state when the input voltage (the voltage of the electrode 38) decays away to less than half of the power supply voltage, the time until this happens $t_0$ will be given approximately by:

$$t_0 = R_{ins}C_{ins} \ln(2) \quad \text{(equation 2)}$$

(3) With the sensor enable line SEN taken high via the row driver circuit 76 (FIG. 7(d)), sampling circuitry in the column detection circuit 86 is then used to sample the voltage at output OUTC at a time $t_1$ following the time SEL was taken low. This is indicated by the sampling pulse SAM (FIG. 7(g)). The sampling of the voltage signal on OUTC may be implemented by any one of a number of standard means, for example by connecting OUTC to the input of a flip-flop of standard design and using pulse SAM to trigger the flip-flop on the rising edge.

One may now consider the case of the operation of the array element circuit 84 when no insulator pinhole defect is present in the insulator layer 20. With all timing signals applied identically to as above, the operation differs in that the voltage applied to the electrode 38 no longer leaks away. Typically in this case the resistance $R_{ins}$ will assume a very large value Giga-ohms or greater. Since the voltage at electrode 28 is maintained (neglecting small leakages through the TFT circuit components which are typically several orders of magnitude smaller than the current associated with an insulator pinhole defect) the inverter 96 will not change state.

Therefore it can be seen that by measuring the logic state of OUTC at time $t_1$ following the SEL falling edge we have effectively implemented a 1-bit measurement of the insulator resistance $R_{ins}$. If $R_{ins}$ is below a certain threshold resistance $R_c$ then the sampled output will be at logic low level. If $R_{ins}$ is above the threshold resistance $R_c$ then the sampled output will be at logic high level. The value of $R_c$ is given by:

$$R_C = \frac{t_1}{C_{ins}\ln 2} \quad \text{(equation 3)}$$

A typical insulator pinhole defect is found to have a resistance of order 10 kilo-ohms (kohm)-10 mega-ohms (Mohms). For typical values of $C_{ins}$, such insulator pinhole defects can be detected by choosing time $t_1$ to be of order of a few to a few tens of milliseconds. Since all the array elements within the same row can all be measured simultaneously, it thus becomes possible to scan the whole of a large AM-EWOD array for insulator pinhole defects in times of typically less than a second.

Since the capacitance $C_{ins}$ is generally known (since the insulator and hydrophobic layer thickness and composition are set by the manufacturing process), by making multiple measurements with different $t_1$, it is possible to determine the insulator resistance associated with a particular insulator pinhole defect. One possible implementation of this embodiment is therefore to make multiple measurements with different sampling time $t_1$. The insulator pinhole defects detected in each case may thus be classified according to the range of resistance values within which they lie.

It may be noted that operation of the measure circuitry relies on the presence of a droplet 4 to complete the circuit and facilitate the measurement of the insulator layer resistance. This may be accomplished by first moving a droplet 4 to the particular array element via a write operation prior to carrying out a measure operation.

It may be noted that it is also possible to perform the measure operation with reversed polarities of voltage on the top and bottom electrodes, e.g. with the electrode 38 voltage programmed low and the top electrode 28 voltage programmed high. In this case the presence of an insulator pinhole defect will cause the output of the inverter 96 to transition from high to low.

It may further be noted that the circuitry components associated with testing for pinhole defects in the insulator (i.e, the inverter 96, transistor 98, the output connection OUTC and the input connection SEN) may also be used for a secondary function of verifying the correct operation of the voltage write circuitry. For example, consider the case where there is no droplet 4 present at the electrode 38. The correct operation of the voltage write circuitry may be verified by the following two procedures:

Firstly, when logic high is written to the SRAM circuit 88 and input line SEL is taken high, a high voltage level is written to the electrode 38. Since the input of inverter 96 is high, the output of the inverter 96 is low. By applying a voltage high pulse to the gate of transistor 98 a low voltage level will appear on the output connection OUTC which may then be sampled as previously described.

Secondly, when logic low is written to the SRAM circuit 88 and input line SEL is taken high, a low voltage level is written to the electrode 38. Since the input of inverter 96 is low, the output of the inverter 96 is high. By applying a voltage high pulse to the gate of transistor 98 a high voltage level will appear on the output connection OUTC which may then be sampled as previously described.

By verifying that the operation as described above (i.e. that the output line OUTC is the logical inverse of the written state of the SRAM), for each element in the array in turn one is able to verify the correct operation of the voltage write circuitry n the absence of any liquid droplets present on the array. Any errors in the voltage write circuitry are therefore detectable in a straightforward manner without the need to input fluid onto the array. Such errors could occur for example in the row driver circuit 76, the column driver circuit 78 or the SRAM circuit 88. These errors may include errors due to an imperfect manufacturing yield, e.g. due to defective transistors, breaks in connecting wires, etc. or to other causes such as incorrect operating voltages, incorrect operating timings, bad electrical connection to the substrate or circuit design errors.

By performing a test of the circuit electronics in this manner, any errors may therefore be detectable in a very straightforward manner without the need to input fluid onto the array.

The advantages of this embodiment are as follows:
By measuring the occurrence of insulator pinhole defects an integrity check is performed on the chemical or biochemical assay being undertaken. The occurrence of an insulator pinhole defect during the assay may be used to indicate the results of the assay as being unreliable.
By varying the time for which the voltage at the array element is sampled, the electrical resistance associated with a particular insulator pinhole defect may be quantified. Since the resistance is directly related to the degree to which electrolysis will occur, this provides further information as to whether the chemistry of the affected droplet 4 has been significantly compromised or not.
By continuous or repeated sampling of the insulator integrity over time the evolution of insulator pinhole defects in real time can be monitored. This may be important since in practise insulator pinhole defects may not occur immediately at affected locations. The fact that a given portion of insulator if functioning correctly at a certain time does not necessarily imply it will function correctly at a later time.
The electronic circuitry used for detecting pinhole defects may also perform the secondary function of testing the electrical integrity of the voltage write function to each element within the array.

Figure 8:
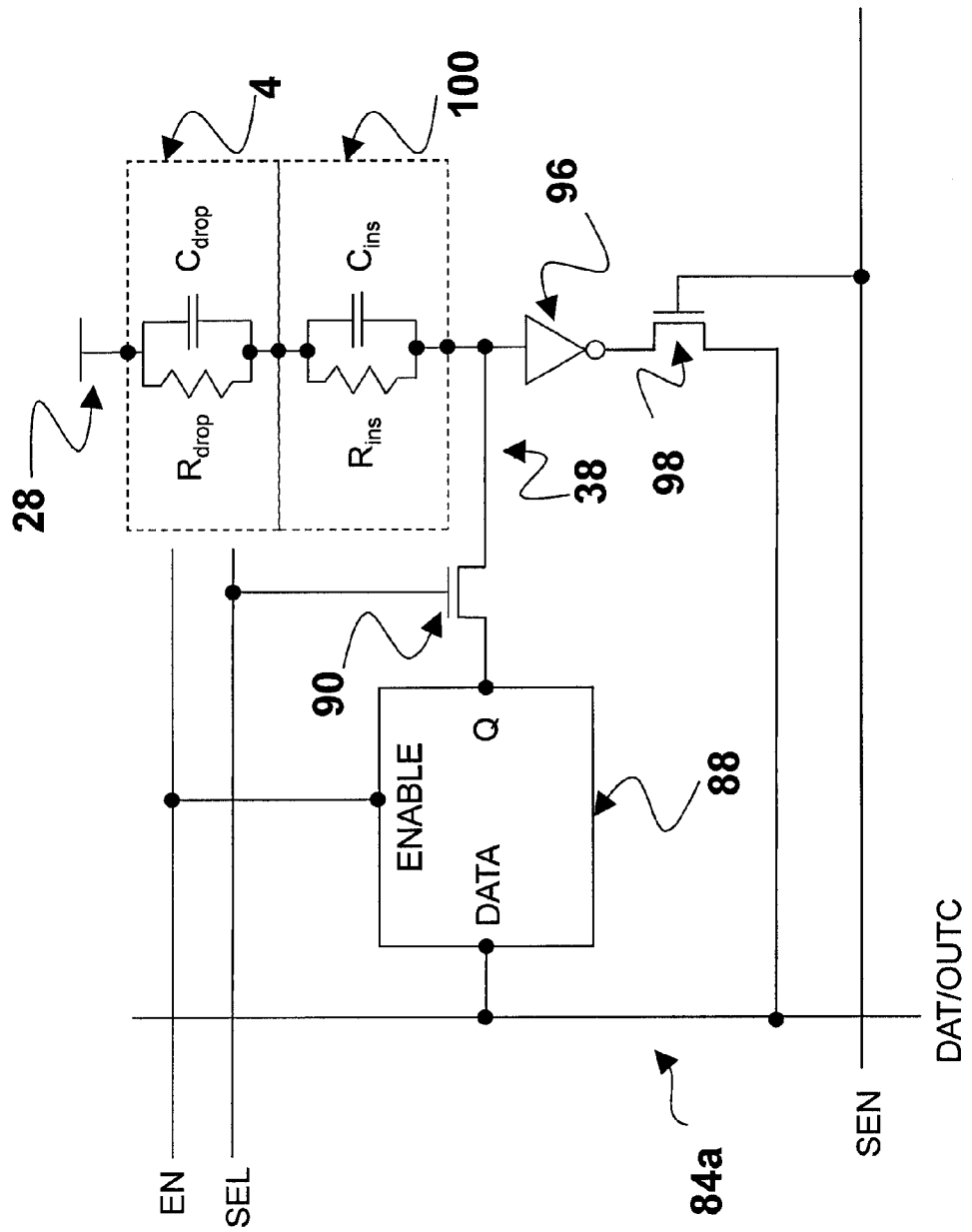
FIG. 8 shows the array element circuit 84 of a second embodiment of the invention.

The AM-EWOD device according to a second embodiment of the invention is as the first embodiment with an alternative array element circuit 84a. The array element circuit 84a of this embodiment is shown in FIG. 8. This differs from the array element circuit 84 of the first embodiment in that the output line OUTC is removed and the input line DAT is replaced by a dual function input/output line DAT/OUTC. The line DAT/OUTC is connected to the source of transistor 98 and to the input DATA of the SRAM circuit 88. The operation of the second embodiment is similar to that of the first embodiment except that the data input of the write operation and the output of the measurement operation share the signal line DAT/OUTC.

An advantage of the second embodiment is that it saves a signal line in comparison to the first embodiment. This has the advantage of reducing the minimum achievable layout footprint of the array element circuit 84a. This may facilitate increased spatial resolution of the array. The reduction by one of the number of connecting wires may also facilitate improved manufacturing yield.

Figure 9:
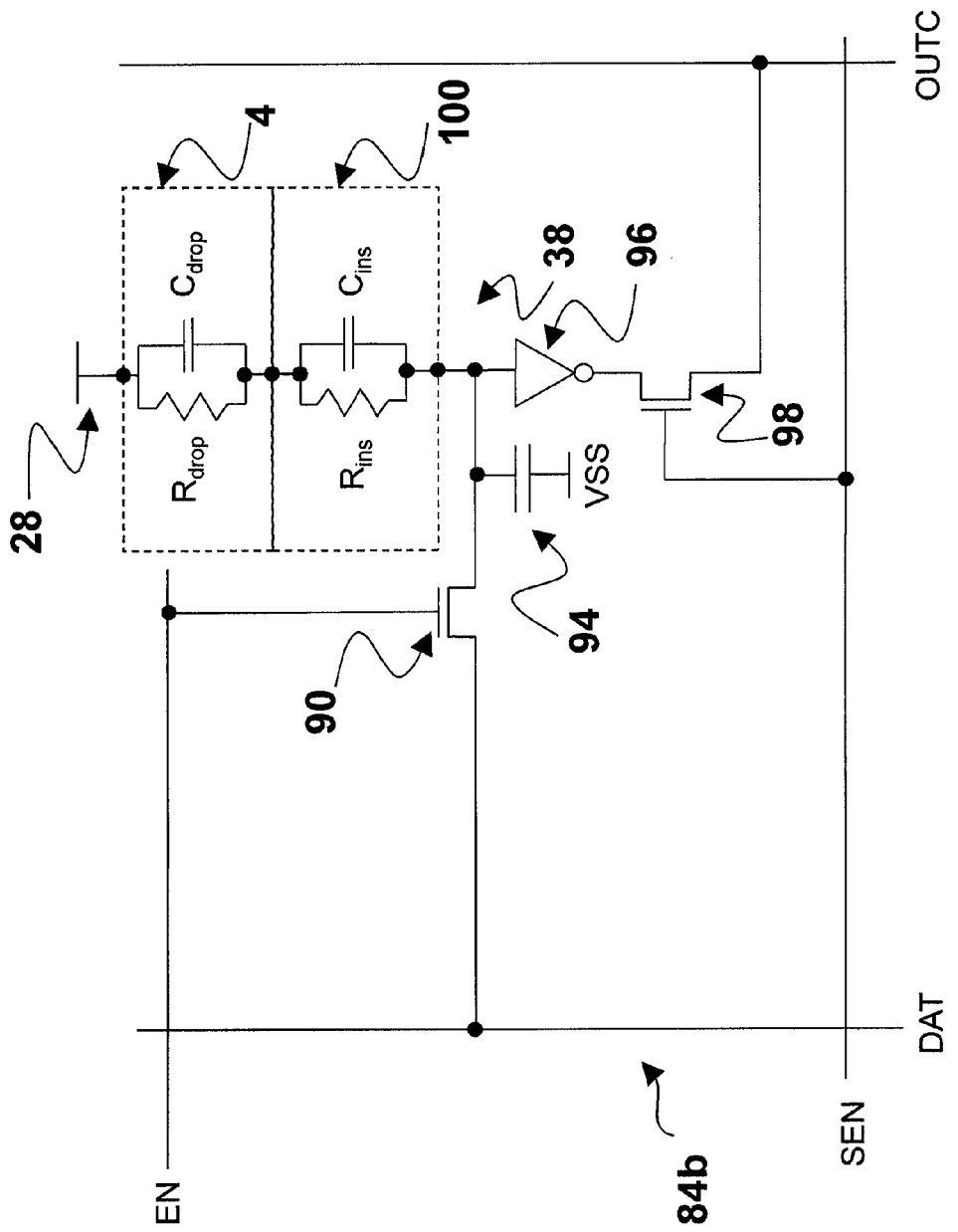
FIG. 9 shows the array element circuit 84 of a third embodiment of the invention.

The AM-EWOD device according to a third embodiment is as the first embodiment with an alternative array element circuit 84c. The array element circuit 84c of this embodiment is shown in FIG. 9. This differs from the array element circuit 84 of the first embodiment as follows:

The SRAM element is removed from the circuit, and the source of transistor 90 is connected to the data input line DAT The select line SEL is removed and the gate of transistor 90 is connected to the enable line EN An additional capacitor 94 of value $C_s$ is connected between the electrode 38 and the low level power supply VSS The operation of the array element circuit 84c is very similar to the first embodiment, except that the voltage write function is implemented by means of a conventional DRAM circuit comprising transistor 90 and capacitor 94. In order to program a write voltage to the electrode 38, a write voltage $V_P$ is provided to the data input line DAT. The enable signal EN is then taken high to switch transistor 90 on. The programmed voltage $V_P$ is then stored on capacitor 94. The operation of the measurement function is then as described for the first embodiment, the only differences being that the written voltage starts to decay when EN is taken low and that there is an additional capacitor 94 of value Cs present at the electrode 38. In this case the time evolution of the voltage $V_{EW}(t)$ at the electrode 38 following EN being taken low is given by:

$$V_{EW}(t) = V_P \exp\left(\frac{-t}{R_{ins}(C_{ins} + C_s)}\right). \quad \text{(equation 4)}$$

An advantage of the third embodiment in comparison to the first embodiment is that it requires fewer circuit components to implement. This has benefits in reducing the minimum array element size that can be achieved and in increasing manufacturing yield. A further advantage of this embodiment is that the voltage that can be programmed to the electrode 38 is not constrained to one of logic high or logic low levels, but may take an arbitrary value V. This facilitates the additional possibility that the threshold resistance $R_c$ can be made to vary as a function of $V_P$ as well as or instead of as a function of $t_1$. It can be shown that the threshold resistance in this case is given by:

$$R_C = \frac{t_1}{C_{ins} \ln\left(\frac{2V_P}{VDD}\right)} \quad \text{(equation 5)}$$

where VDD is the high level logic power supply and the low level logic power supply is 0V. This means of providing additional flexibility in defining $R_c$ facilitates relatively high values of threshold resistance $R_c$ to be defined without requiring $t_1$ to be set to a value which is impractically high.

Figure 10:
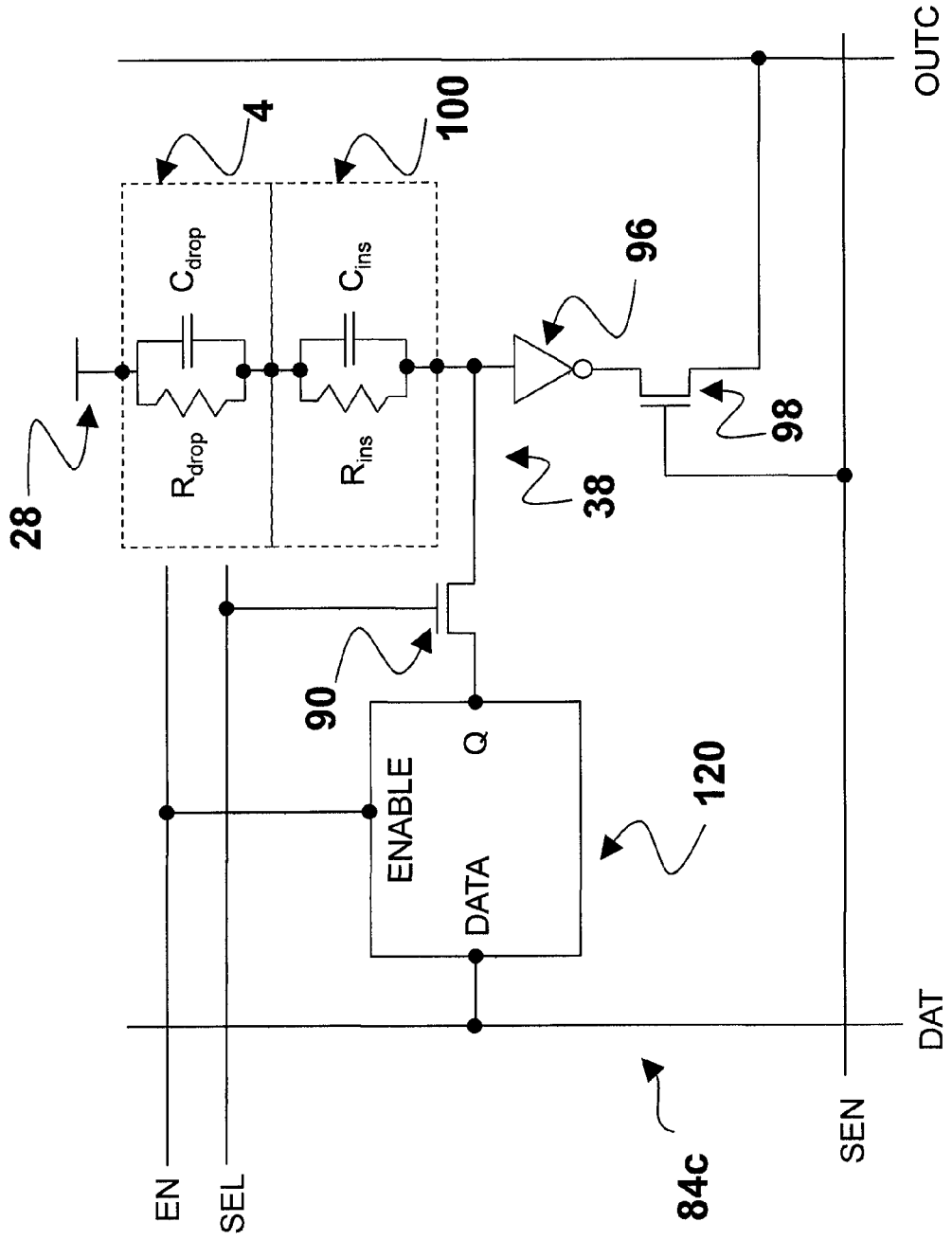
FIG. 10 shows the array element circuit 84 of a fourth embodiment of the invention.
Figure 11:
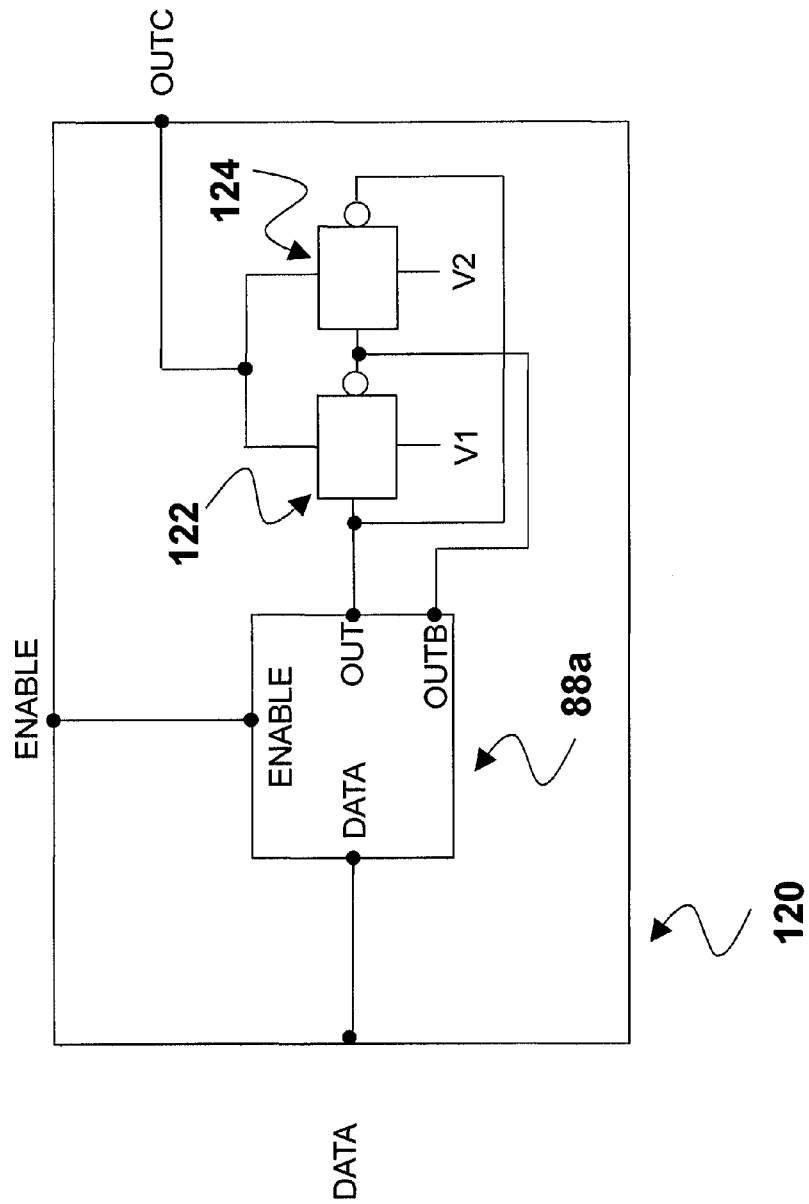
FIG. 11 shows the voltage write circuitry of the fourth embodiment of the invention

A fourth embodiment of the invention is shown in FIG. 10. This embodiment is as the first embodiment except that in the array element circuit 84c the SRAM element 88 is replaced by voltage write circuitry 120. The voltage write circuitry 120 is shown in FIG. 11 and contains the following elements:

An SRAM circuit 88 of standard construction (e.g., as described above), having DATA and ENABLE inputs and outputs Q and Q-bar (identified as OUT and OUTB, respectively).

An analogue switch 122

A second analogue switch 124 The connectivity of the voltage write circuitry 120 within the array element is as follows:

The input DAT is connected to the input DATA of the voltage write circuitry 120 which is connected to the input DATA of the SRAM circuit 88a. The SRAM circuit 88a is that of the second embodiment discussed above, with the addition of a complementary output. The input line EN is connected to the input ENABLE of the voltage write circuitry 120 which is connected to the input ENABLE of the SRAM circuit 88a. The output OUT of the SRAM circuit 88a is connected to the gate of the n-type transistor of analogue switch 122 and to the gate of the p-type transistor of analogue switch 124. The inverted output OUTB of the SRAM circuit 88a is connected to the gate of the p-type transistor of analogue switch 122 and to the gate of the n-type transistor of analogue switch 124. A voltage signal V1 is connected to the input of analogue switch 122. A voltage signal V2 is connected to the input of analogue switch 124. The output of analogue switch 122 is connected to the output of the analogue switch 124 which is connected to the terminal OUTC of the voltage write circuitry 120 (labeled as "Q" in FIG. 10), which is connected to the source of transistor 90. The voltage signal V2 is also connected to the electrode 28 of the top substrate 36. The input DAT and output OUTC may be common to all array elements in the same column of the array 42. The input lines EN, SEL and SEN may be common to all array elements within the same row of the array 42.

The voltage write circuitry 120 operates as follows. The SRAM circuit 88 is programmed in the same way as described for the first embodiment by means of the DATA and ENABLE inputs. In the case where the SRAM circuit 88 is programmed to the "1" state, output OUT is logic high and output OUTB is logic low. Accordingly analogue switch 122 is switched on, analogue switch 124 is switched off and when transistor 90 is switched on the voltage signal V1 is connected to the electrode 38. Conversely, when the SRAM circuit 88 is programmed to the "0" state, output OUT is logic low, output OUTB is logic high, analogue switch 122 is switched off and analogue switch 124 is switched on so that voltage signal V2 is connected to the electrode 38 when transistor 90 is switched on.

During the write operation, voltage signals V1 and V2 may be either alternating current (AC) or direct current (DC) waveforms appropriate for the manipulation of fluids by means of the electro-wetting effect. Since voltage signal V2 is also be connected to the top substrate electrode 28, writing the SRAM circuit 88 to "1" corresponds to a voltage V1-V2 being developed between the electrode 38 and top substrate electrode 28 of a given array element, whilst writing the SRAM circuit 88 to "0" corresponds to a voltage V2-V2=0 Volts being developed between the electrode 38 and top electrode 28. These may correspond to the actuated and non-actuated states respectively, and by setting V1 to a squarewave waveform and V2 to a corresponding squarewave that is the antiphase of V1, an AC method of electrowetting actuation may be implemented.

During the measure operation, V1 may be set to a high voltage DC waveform, e.g. V1=$V_P$ and V2 to a low voltage DC waveform, e.g. 0V. The measure operation is the implemented by writing "1" to the SRAM circuit of the voltage write circuitry 120 and switching on transistor 90 in order that DC voltage $V_P$ is supplied between the electrode 38 and top substrate electrode 28. The measure operation then proceeds in an identical way to as has been previously described, commencing with the select signal line SEL being taken low to switch off transistor 90.

An advantage of this embodiment is that it combines the basic concept of measuring the location and resistance of insulator pinhole defects with the capability to operate the AM-EWOD with an AC drive scheme. A further advantage of this embodiment is that the voltage $V_P$ that is programmed to the electrode 38 at the start of the measure operation may be any value and is not constrained to the power supply voltages. This facilitates the additional possibility that the threshold resistance $R_c$ can be made to vary as a function of $V_P$ as well as or instead of as a function of $t_1$, as described for the third embodiment.

A fifth embodiment of the invention is identical to the fourth embodiment except that a third voltage signal V3 is instead connected to the electrode 28 of the top substrate 26 in place of the voltage signal V2. The operation of this embodiment is as follows: the write operation is performed in an identical way as described for the fourth embodiment, with the voltage signal V3 being set equal to the voltage signal V2.

In order to perform the measure operation, both voltage signals V1 and V2 are set to a high level DC voltage=$V_P$, whilst voltage signal V3 is set to a low level DC voltage (e.g. 0V). When transistor 90 is turned on, the electrode voltage 38 is then set to $V_P$, regardless of the state of the programmed state of the SRAM circuit 88. The measure operation then proceeds in an identical way to as has been previously described, commencing with the input signal SEL being taken low to switch off transistor 90.

This embodiment has all the advantages of the fourth embodiment, plus an additional advantage that in order to perform the measure operation, it is not necessary to first re-program the SRAM circuit 88. This has the beneficial effect of speeding up the measure operation, and also in preserving programmed data written to the array and stored in the SRAM circuits 88 of each array element.

Figure 12:
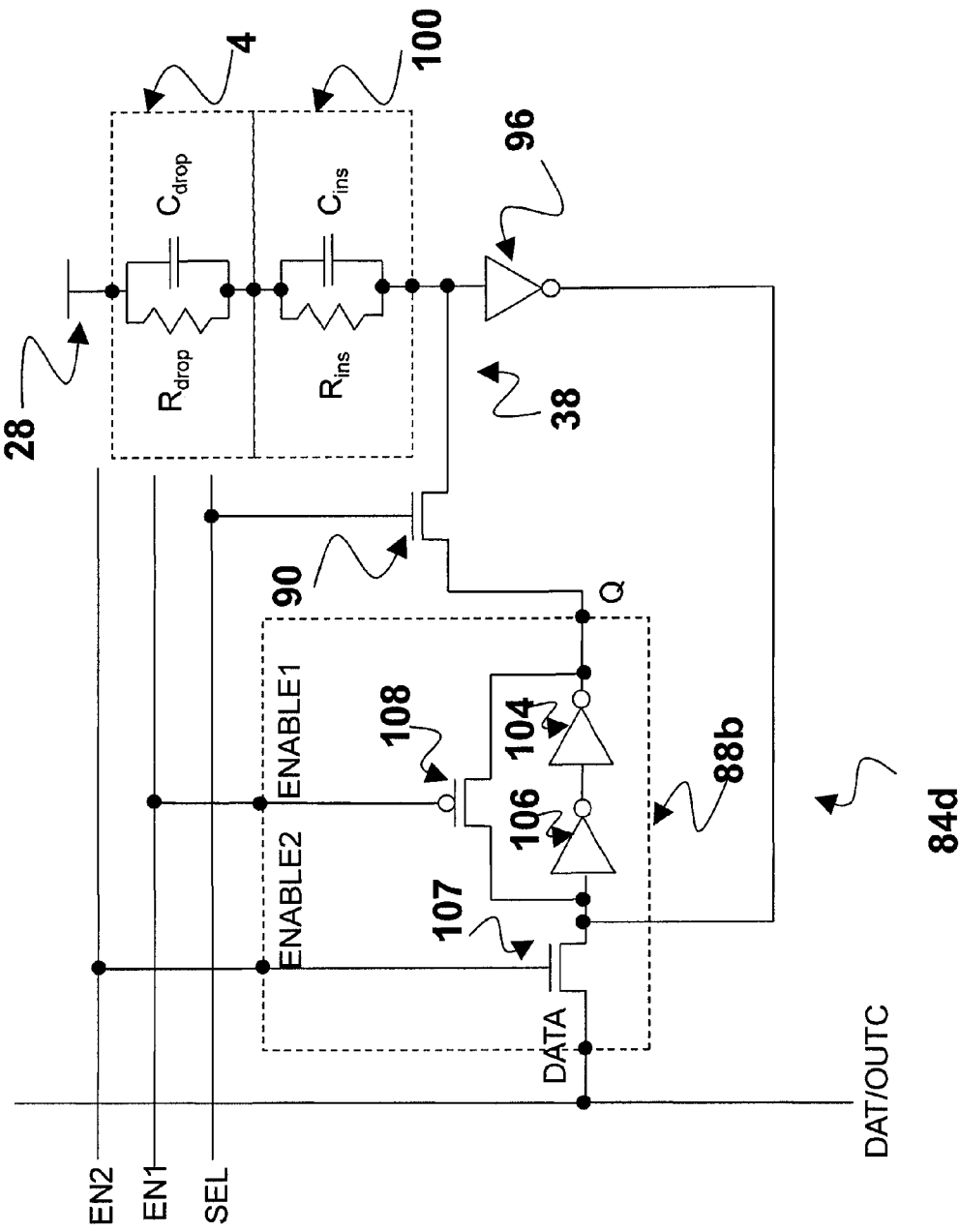
FIG. 12 shows the array element circuit 84 of a sixth embodiment of the invention.

A sixth embodiment of the invention is shown in FIG. 12. This embodiment is as the second embodiment except that in the array element circuit 84d the switch transistor 98 has been removed and its function implemented by transistor 107 which forms part of the SRAM circuit 88B. The SRAM circuit 88b is also slightly modified in that separate connections are provided to the gates of the switch transistors, the gate of transistor 108 is connected to voltage line EN1 and the gate of transistor 107 being connected to voltage line EN2 (via inputs ENABLE1 and ENABLE2, respectively), with both EN1 and EN2 lines being common to all array elements in the same row of the array 42.

Figure 13:
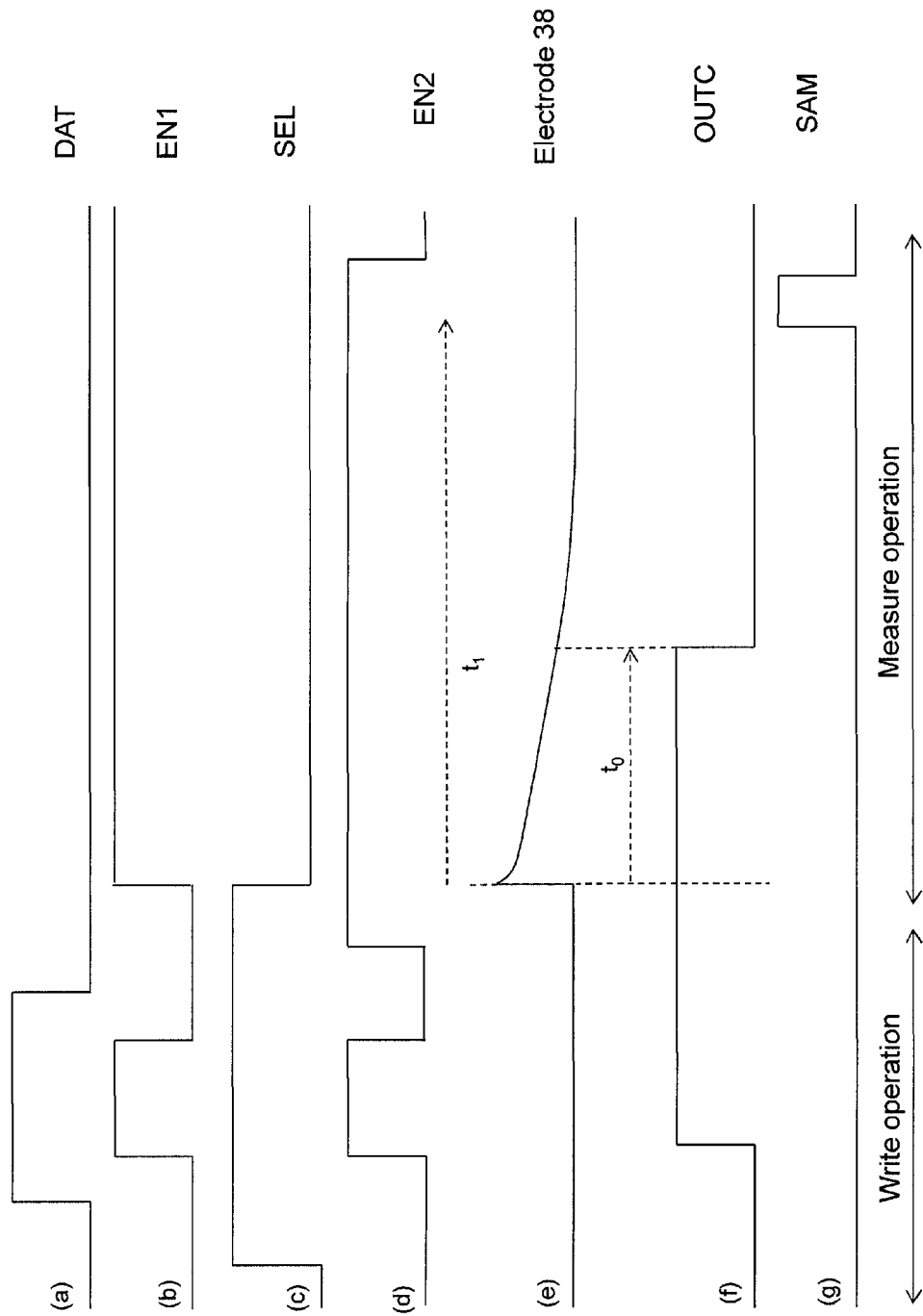
FIG. 13 shows a timing diagram for operation of the array element circuit 84 of the sixth embodiment of the invention.

The operation of the array element circuit 84d is similar to that described for previous embodiments, and may be described with reference to the timing circuit showing in FIG. 13. To perform the write operation, both EN1 and EN2 (FIGS. 13(b) and 13(d), respectively) are taken high row driver circuit 76 in order to correctly configure the SRAM circuit 88b to sample and hold the voltage signal on input line DAT (FIG. 13(a)) at the input DATA as previously described. In performing the measure operation, the transistor 107 becomes shared by the measure circuitry and fulfills the function previously fulfilled by transistor 98 (in accordance with the second embodiment), namely in switching the output of the inverter 96 to the input/output line DAT/OUTC. As shown in FIG. 13, SEL (FIG. 13(c)) is taken low and EN1 taken high by the row driver circuit 76 simultaneously at the start of the measure operation. This has the effect of turning transistor 108 off at the start of the measure operation and disconnecting the feedback loop in the SRAM circuit 88*b*. Therefore from the time SEL is taken low by the row driver circuit 76, the potential at the drain of transistor 107 is controlled solely by inverter 96; inverter 104 having been disconnected from this node.

The sixth embodiment has the advantages of the second embodiment plus the additional advantage that one transistor has been removed from the circuit. This has the advantages of reducing layout footprint (and enabling increased resolution) and may also facilitate improve manufacturing yield.

Figure 14:
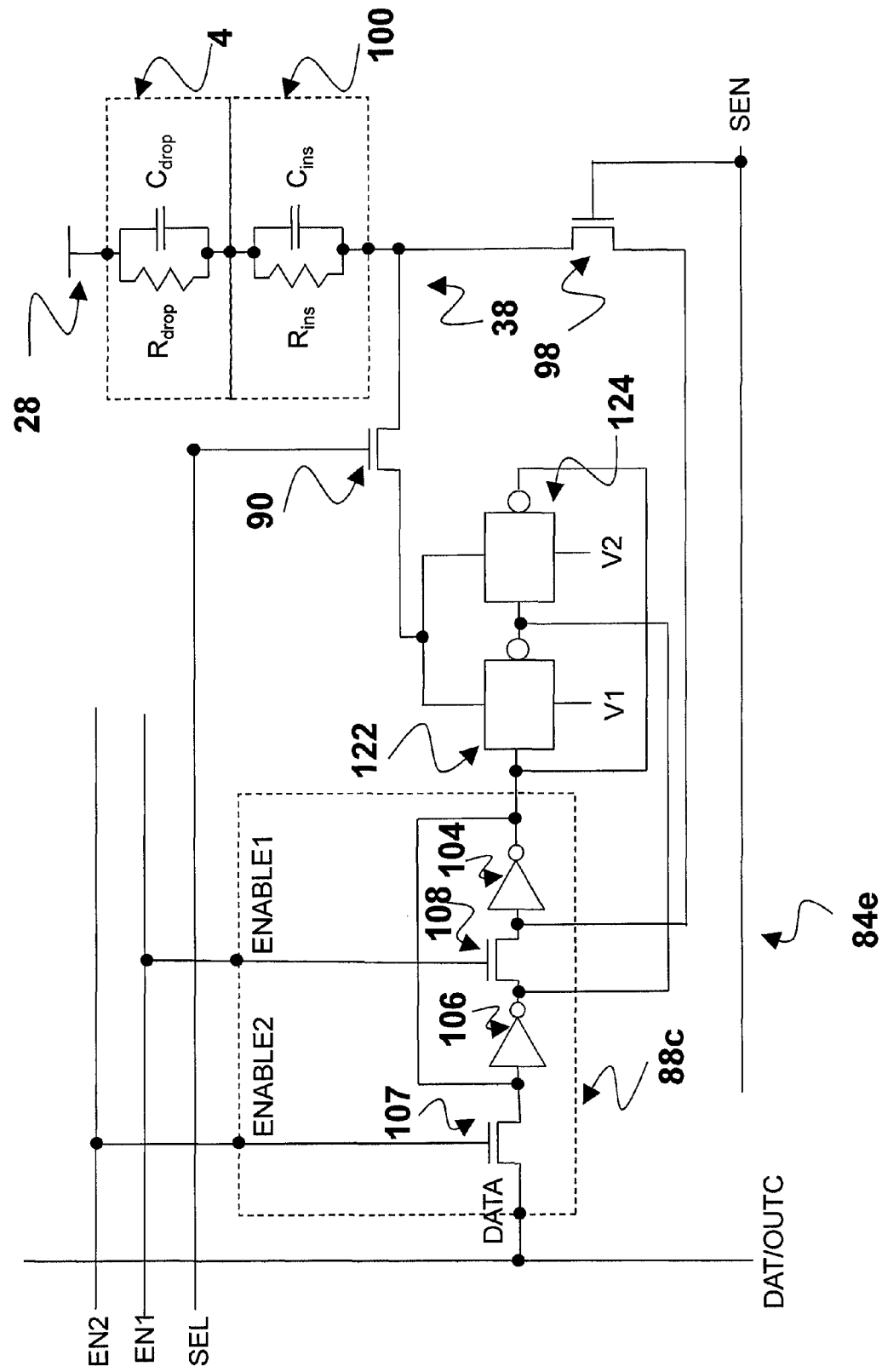
FIG. 14 shows the array element circuit 84 of a seventh embodiment of the invention.

A seventh embodiment of the invention is as the first embodiment with an array element circuit 84*e* as shown in FIG. 14.

The array element circuit 84*e* contains the following elements

An n-type transistor 107
    An n-type transistor 108
    An inverter 106
    An inverter 104
    An analogue switch 122
    An analogue switch 124
    An n-type transistor 90
    An n-type transistor 98

The array element circuit 84*e* is connected as follows:

In an SRAM circuit 88*c*, the source of transistor 107 is connected to the input/output line DAT/OUTC which may be common to all array elements in the same column of the array 42. The gate of transistor 107 is connected to the input line EN2 via input ENABLE2. The drain of transistor 107 is connected to the input of inverter 106, to the output of inverter 104, to the gate of the n-type transistor of analogue switch 122 and to the gate of the p-type transistor of analogue switch 124. The output of inverter 106 is connected to the source of transistor 108, to the gate of the p-type transistor of analogue switch 122 and to the gate of the n-type transistor of analogue switch 124. The drain of transistor 108 is connected to the source of transistor 98 and to the input of inverter 104. The gate of transistor 108 is connected to the input line EN1 via the input ENABLE1. Input voltage signal V1 is connected to the input of analogue switch 122. Input voltage signal V2 is connected to the input of analogue switch 124. The output of analogue switch 122 is connected to the output of analogue switch 124 and to the source of transistor 90. The gate of transistor 90 is connected to the select signal line SEL. The drain of transistor 90 is connected to the electrode 38 and to the drain of transistor 98. The gate of transistor 98 is connected to the sense enable input line SEN. Each of input lines EN1, EN2, SEL and SEN may be common to array elements in the same row of the array 42.

Figure 15:
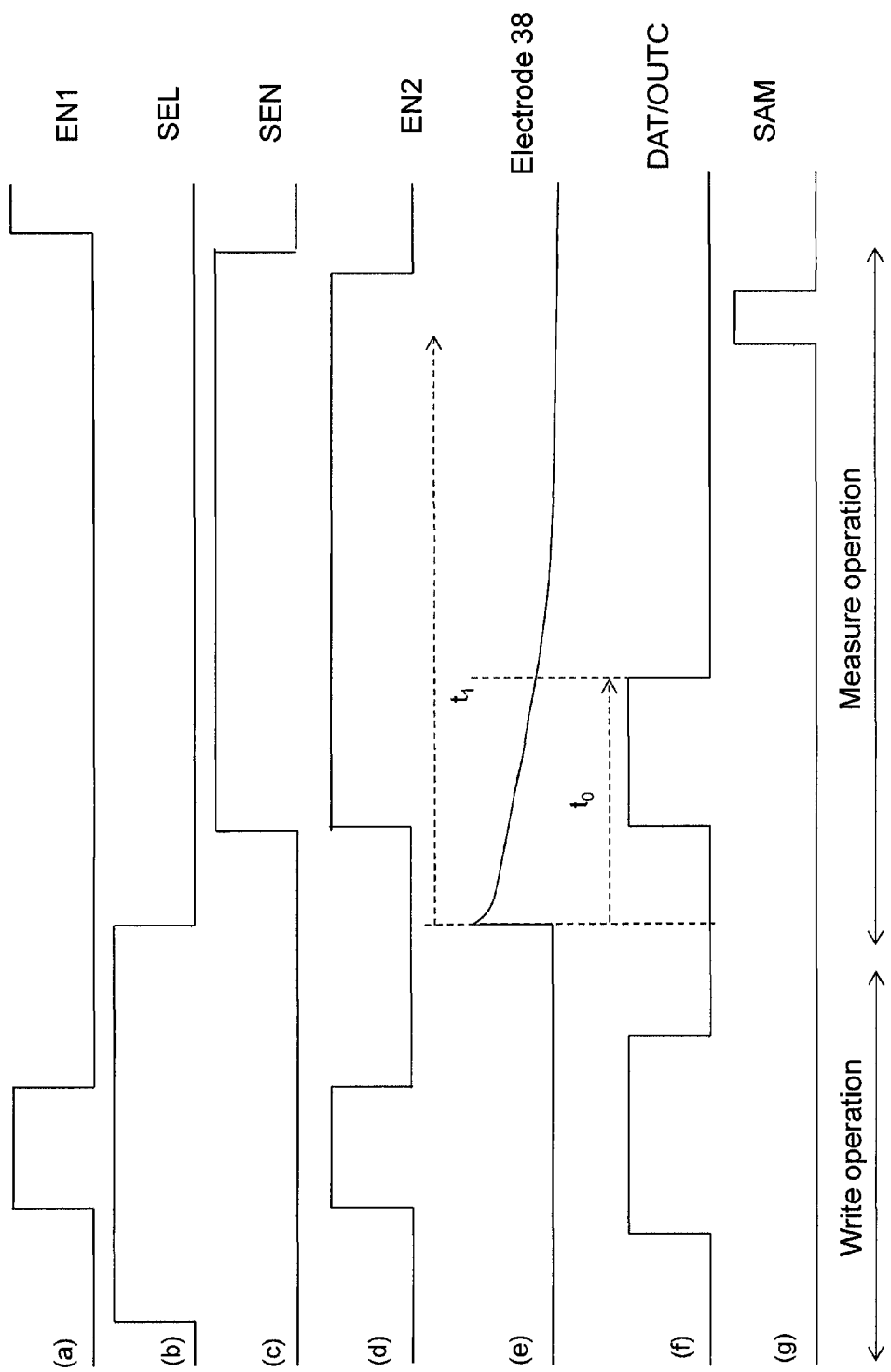
FIG. 15 shows a timing diagram for operation of the array element circuit 84 of the seventh embodiment of the invention.

The operation of the array element circuit 84*e* of this embodiment is as follows, described with reference to the timing diagram shown in FIG. 15. To perform the write operation, data to be stored in the SRAM circuit 88*c* is programmed by means of the DAT/OUTC line and the EN1 and EN2 lines (FIGS. 15(*f*), 15(*a*) and 15(*d*), respectively) as previously described. The programmed state of the SRAM circuit 88*c* then determines which of the analogue switches 122 or 124 is turned on, and hence whether V1 or V2 is connected to the electrode 38 when transistor 90 is turned on. To perform the measure operation, the electrode is first written to a high voltage state, with the voltage on the top substrate electrode 28 maintained at a low voltage so as to maintain an electric field across the insulator layer 20 as previously described. SEL is then taken low to switch off transistor 90 (FIG. 15(*b*)). From this point, charge may start to leak away from the electrode 38 in the case where the insulator layer 20 contains an insulator pinhole defect. EN1 is then taken low to open the feed-back loop of the SRAM circuit 88*c*. SEN is then taken high and the electrode 38 becomes connected to the input of inverter 104 (FIG. 15(*c*)). Inverter 104 now performs the same function that inverter 96 performed in the first embodiment, namely measuring the voltage at the electrode 38. The output of inverter 104 changes state if and when the voltage of the electrode 38 drops to below approximately the logic mid-rail voltage as previously described. By taking EN2 high (which for example could be arranged to occur at the same time SEN is taken high, as shown in FIG. 15(*d*)) the output of inverter 104 is switched to the DAT/OUTC line from where it may be sampled as previously described.

This embodiment has the advantages of the fourth embodiment, plus the additional advantage that the measurement function is implemented with the addition of a single additional switch transistor (transistor 98) and sense enable line (SEN). This is achieved by the use of a slightly modified SRAM circuit 88*c* arranged such that inverter 104 becomes shared and performs a dual function; i.e. by forming part of an SRAM memory cell in the write circuitry during the write operation, and by acting as a readout device in the measure circuitry during the measure operation. It may be noted that a disadvantage of this embodiment compared to the fourth embodiment, is that write information programmed to the SRAM circuit 88*c* is by necessity lost when a measure operation is performed, and therefore following the measure operation the array element is required to be re-programmed.

Figure 16:
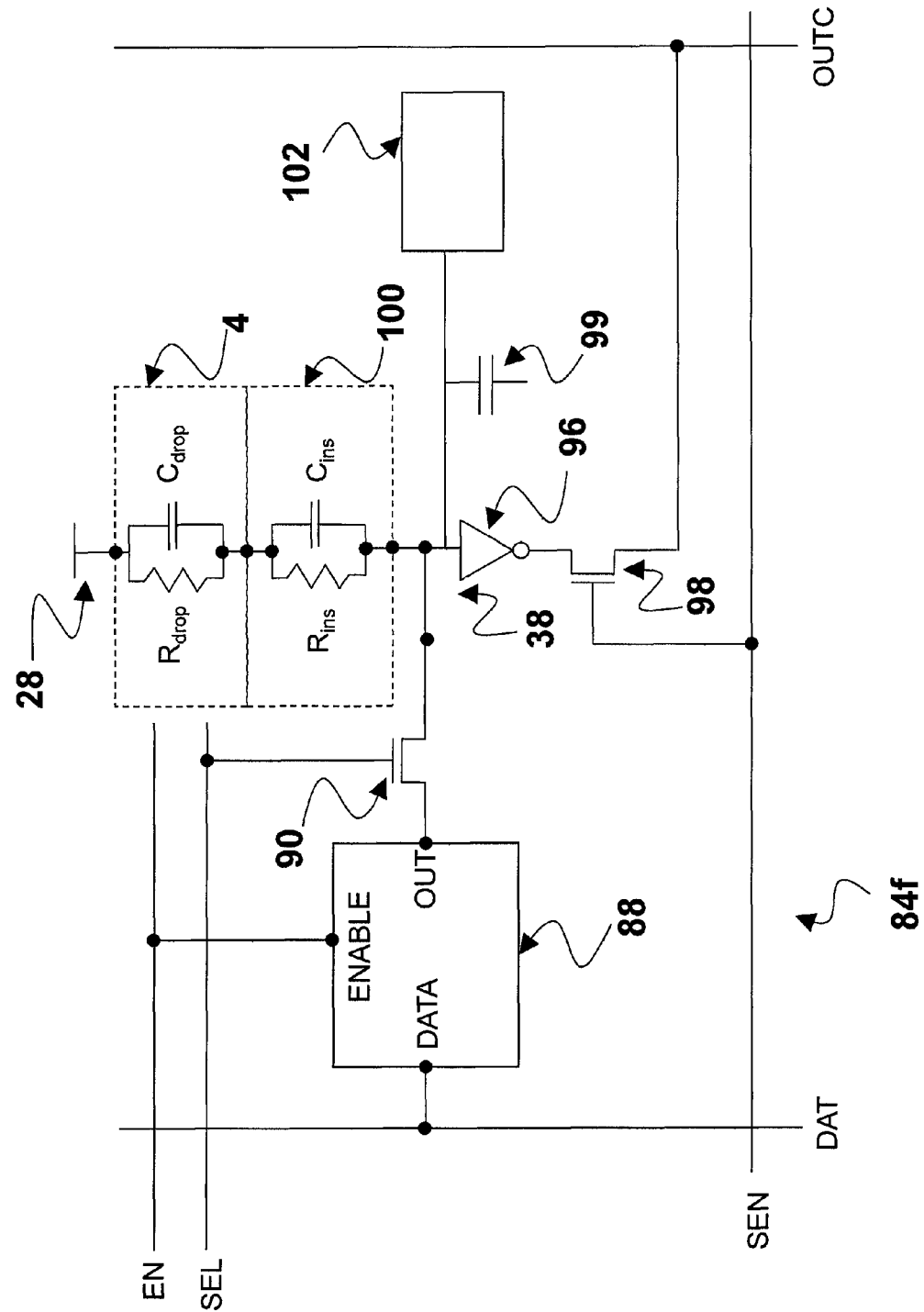
FIG. 16 shows the array element circuit 84 of an eight embodiment of the invention.

An eighth embodiment of the invention is shown in FIG. 16. This embodiment is as the first embodiment except that an additional droplet sensor circuit 102 is connected to the electrode 38. The droplet sensor circuit 102 functions to sense the presence of one or more droplets 4 within the array element. The droplet sensor circuit 102 may be of a type as known and described in the conventional art, for example based on sensing the electrical impedance present at the electrode 38. The operation of such a droplet sensor circuit 102 is described in the conventional art and may essentially function independently of the measurement of the resistance of the insulator layer 20 described in this invention. In performing the measure operation in accordance with the array element circuit 84*f* of this embodiment, the only difference with the first embodiment is that the presence of the droplet sensor circuit 102 may result in additional capacitance $C_n$ being present at the electrode 38, as represented by the capacitor 99 if FIG. 16. Thus in the analysis of the operation of the array element circuit 84*f* of this embodiment, the term $C_{ins}$ is replaced by $C_{ins} C_n$ in equations (1) to (3), in all other respects the operation of the measure operation being identical to as previously described.

It will be apparent to one skilled in the art how the droplet sensor function of the droplet sensor circuit 102 could also be combined with the second to seventh embodiments.

Figure 17:
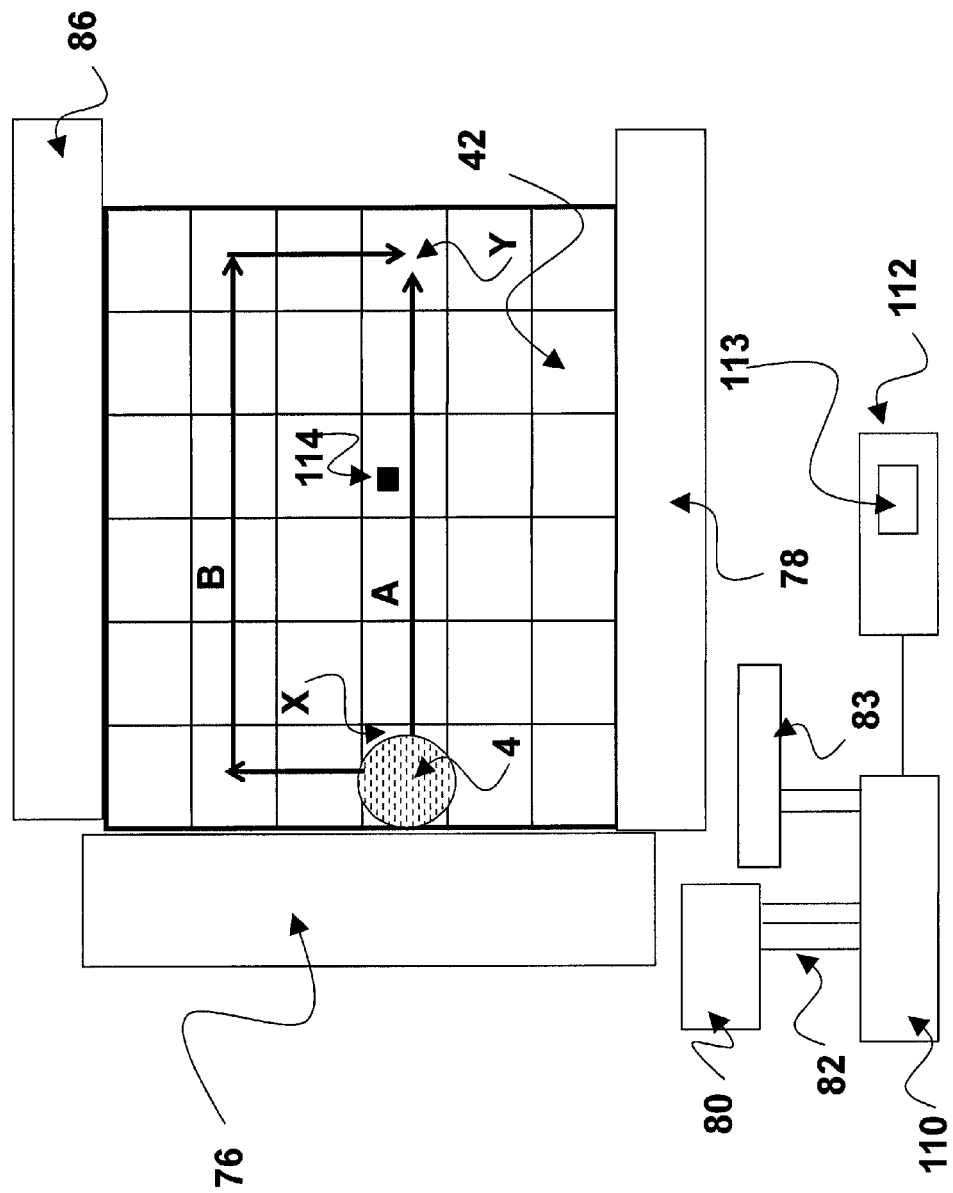
FIG. 17 shows a ninth embodiment of the invention.

A ninth embodiment of the invention is shown in FIG. 17. This embodiment demonstrates a system implementation of any of the previous embodiments, showing how the AM-EWOD device may be dynamically re-programmed in accordance with the measured occurrence and location of insulator pinhole defects as described above. The figure shows an AM-EWOD device, with control signals (voltage waveforms, power supply voltages and so on) as required to drive the device being supplied from external electronics 110, e.g. a Printed Circuit Board (PCB). The timing signals representing the data pattern programmed to the AM-EWOD are in turn controlled by a computer controller 112 running application software 113. The application software 113 may also be configured to receive and interpret measurement data sent via the external electronics 110 and representing the occurrence and location of insulator pinhole defects on the AM-EWOD device and to store in memory the location of detected insulator pinhole defects.

An example operation of the embodiment is also shown in FIG. 17. Suppose that the application software 113 issues a command to the device to move a liquid droplet 4 from location X to Y. This move operation could for example form part of a biochemical assay being performed by the device. Before implementing the move operation, the application software determines the route through the array to be followed by the liquid droplet 4. This may be implemented for example by path finding algorithms of standard means. Suppose that during a previous droplet operation, the measure option detected an insulator pinhole defect at the location indicated 114 in FIG. 17. According to this embodiment, the application software 113 will account for the presence of the insulator pinhole defect location 114 and compute a route for the liquid droplet 4 to follow accordingly. For example, in the situation shown in the figure, the liquid droplet 4 will be commanded to follow the route indicated by the arrows B to traverse from X to Y, avoiding the insulator defect location 114. Had the insulator pinhole defect not been present in this location, the liquid droplet 4 would have instead followed the route indicated by the arrow A. Such reconfiguration of the device in accordance with measured insulator pinhole defects may also take the form of any of the following:

- Repeating one or more biochemical assays in the case where the occurrence of an insulator pinhole defect was detected during the performance of the assay. This may be necessary to ensure reliable results since the occurrence of the insulator pinhole defect may cause electrolysis in the liquid droplet 4 which may contain sample or reagent, the contamination of which compromise the chemical integrity of the assay
- Repeating one or more steps or sub-steps of a particular assay protocol
- Reporting warnings to an output file of the position and time of occurrence of insulator pinhole defects. This information may then be stored and later retrieved for subsequent usage of the device An advantage of this embodiment is that by incorporating a provision to dynamically reconfigure the device in accordance with the measured occurrence and location of insulator pinhole defects a certain number of such defects can be tolerated without compromising the ability of the device to perform its intended function. The overall effect will be to improve the success rate of the assay and to increase confidence that the results of the assay are reliable. The ability to tolerate a certain number of insulator pinhole defects within the device may also have the overall effect of increasing manufacturing yield of the AM-EWOD device.

Figure 18:
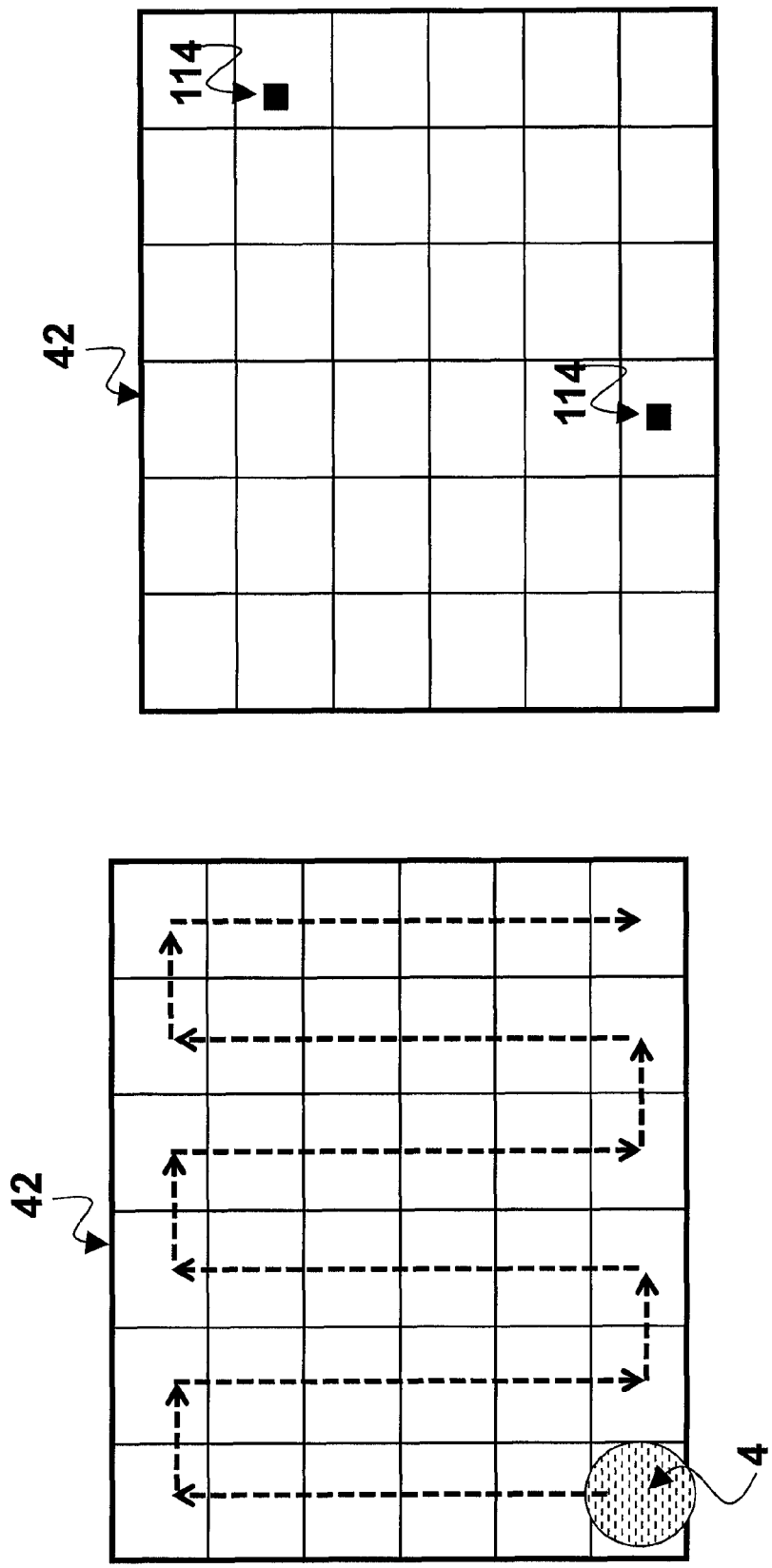
FIG. 18 shows a tenth embodiment of the invention.

A ninth embodiment of the invention is shown in FIG. 18. This embodiment shows a further example system embodiment of any one of the first five embodiments. According to the operation of this embodiment the positions of insulator pinhole defects may be pre-determined prior to performing a biochemical assay, i.e. a pre-test. This may be done by moving a liquid droplet 4 of a saline or buffer solution to each element of the array in turn as shown in the left hand part of FIG. 18. A measure operation is performed at each location. Accordingly a map of the locations of array elements containing an insulator pinhole defect 114 may be created, shown in the right hand part of FIG. 18. This map may then be used to reconfigure the device, as for example described in the sixth embodiment. Such a pre-test could be undertaken immediately prior to performing a biochemical assay. Alternatively it could also be performed in the factory of manufacture and the results used as part of a pass/fail criteria of the suitability of the device. Such a pre-test may also include as an optional additional protocol a pre-test of the voltage write circuitry itself. This may be performed by writing to the electrode 38 of each array element and reading out the voltage written, as described in the first embodiment of the invention.

An advantage of this embodiment is that the position and location of insulator pinhole defects can be determined prior to performing any biochemical assay. The device can therefore be reconfigured in accordance with the results so that the paths followed by the liquid droplets 4 used in assays avoid the affected array elements. The overall effect will be to increase the reliability of the assay.

A further advantage is that the pre-test of this embodiment allows insulator integrity measurements to be performed on the device in the factory of manufacture. The results may be used as part of a pass/fail criteria on the device or to monitor the quality of the insulator process over time.

It will be further apparent that the AM-EWOD device described could form part of a complete lab-on-a-chip system as described in prior art. Within such as system, the droplets sensed and/or manipulated in the AM-EWOD device could be chemical or biological fluids, e.g. blood, saliva, urine, etc, and that the whole arrangement could be configured to perform a chemical or biological test or to synthesize a chemical or biochemical compound.

An aspect of the invention is an AM-EWOD device with an integrated means of detecting insulator pinhole defects that are associated with current passing through the insulator layer at certain discrete locations. An array element circuit operates by measuring an RC time constant associated with the leakage of charge from the electrode through the insulator layer and uses the presence of the liquid droplet 4 to complete the circuit by providing connection to the top substrate electrode 28.

According to another aspect of the invention, by varying the time for which the voltage at the array element is sampled as part of the RC time constant measurement, the electrical resistance associated with the insulator pinhole defect can be measured.

According to a further aspect of the invention the integrity of the insulator layer can be continuously monitored as part of the operation of the AM-EWOD device. Accordingly, the occurrence of electrolysis due to the presence or appearing of insulator pinhole defects can be monitored. This information may then subsequently used to re-program the device and implement corrective actions, for example repeating a biochemical assay whose results may be compromised by the occurrence of electrolysis According to a further aspect of the invention, an AM-EWOD device may be pre-tested prior to use to monitor the position and occurrence of insulator pinhole defects within the device. This pre-test may take the form of running a liquid droplet, comprised for example of a calibration solution or buffer solution, through the array and measuring the insulator integrity at each array element location. Such a pre-test may be implemented immediately prior to the use of the device to perform a biochemical assay, and the results used to designate regions of the array (in the vicinity of insulator pinhole defects) as "out of bounds" for the implementation of the assay. Such a pre-test may also include the pre-testing of the voltage write function (which may be performed prior to introducing liquid droplets to the array). Such a pre-test of the device may also be undertaken in the factory of manufacture, the results of such a pre-test being used to pass or fail the device as suitable for product.

Advantages of the invention include:

By measuring the occurrence of insulator pinhole defects an integrity check is performed on the chemical or biochemical assay being undertaken. The occurrence of an insulator pinhole defect during the assay may be used to indicate the results of the assay as being unreliable.

By measuring the locations of insulator pinhole defects occurring within the array, the device may be dynamically reconfigured such that subsequent droplet operations avoid the affected locations.

By providing a means for detecting insulator pinhole defects, a certain quantity can be tolerated such that the device remains fit for purpose. This may be achieved by suitable design of the array so as to include a degree of redundancy. Specifically, the array may be designed to be of suitable size and sufficient flexibility such that in the event of one or more regions of the device being or becoming inoperable due the occurrence of insulator pinhole defects, the device may be dynamically configured and thus able to repeat droplet operations, biochemical assays or parts thereof as required. This has the overall effect of increasing manufacturing yield, since a certain level of insulator pinhole defects can successfully be tolerated.

By varying the time for which the voltage at the array element is sampled, the electrical resistance associated with a particular insulator pinhole defect may be quantified. Since the resistance is directly related to the degree to which electrolysis will occur, this provides further information as to whether the chemistry of the affected liquid droplet has been significantly compromised or not.

By continuous sampling of the insulator integrity the evolution of insulator pinhole defects in real time can be monitored. This may be important since in practice insulator pinhole defects may not occur immediately at affected locations. The fact that a given portion of insulator if functioning correctly at one time does not necessarily imply it will function correctly at a later time The inclusion of a means for detecting insulator pinhole defects allows insulator integrity measurements to be performed on the device in the factory of manufacture. The results may be used as part of a pass/fail criteria on the device or to monitor the quality of the insulator process over time.

Although the invention has been shown and described with respect to a certain embodiment or embodiments, equivalent alterations and modifications may occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein exemplary embodiment or embodiments of the invention. In addition, while a particular feature of the invention may have been described above with respect to only one or more of several embodiments, such feature may be combined with one or more other features of the other embodiments, as may be desired and advantageous for any given or particular application.

INDUSTRIAL APPLICABILITY

The AM-EWOD device could form a part of a lab-on-a-chip system. Such devices could be used in manipulating, reacting and sensing chemical, biochemical or physiological materials. Applications include healthcare diagnostic testing, chemical or biochemical material synthesis, proteomics, tools for research in life sciences and forensic science.

The invention claimed is:

1. A method of manipulating one or more droplets of fluid on an array, using a plurality of array elements included in an active matrix electrowetting on dielectric (AM-EWOD) device, each of the array elements including a corresponding array element circuit, the method comprising:

writing data to the array element using a write circuitry included in the array element circuit, with an insulator layer being interposed between the one or more droplets and a drive electrode; and checking an integrity of the insulator layer using a measure circuitry included in at least some of the array element circuits to detect pinhole defects in the insulator layer prior to an assay being undertaken with the device.

2. The method according to claim 1, comprising:
monitoring an evolution of pinhole defects in the insulator layer by continuous or repeated checking of the insulator layer over time using the measure circuitry to detect pinhole defects.

3. The method according to claim 1, comprising:
varying a voltage which is written to the drive electrode in order to detect the pinhole defect in the insulator layer.

4. The method according to claim 1, comprising:
detecting pinhole defects in the insulator layer, using the measure circuitry, without rewriting write data to the array element.

5. The method according to claim 1, comprising:
detecting pinhole defects in the insulator layer with the measure circuitry; and
determining a route by which to manipulate the one or more droplets taking into account the detected pinhole defects.

6. The method according to claim 1, comprising:
creating a map of array elements which include a pinhole defect.

7. The method according to claim 1, comprising:
detecting pinhole defects in the insulator layer in a factory of manufacture, using the measure circuitry.

8. The method according to claim 1, comprising;
verifying operation of the write circuitry, using the measure circuitry.

* * * * *